United States Patent
Hoveyda et al.

(10) Patent No.: US 11,478,472 B2
(45) Date of Patent: Oct. 25, 2022

(54) NK-3 RECEPTOR ANTAGONISTS FOR THERAPEUTIC TREATMENT OF LEPTIN-RELATED DISEASE

(71) Applicant: OGEDA SA, Charleroi (BE)

(72) Inventors: Hamid Hoveyda, Brussels (BE); Graeme Fraser, Bousval (BE)

(73) Assignee: Ogeda SA, Vilvoorde (BE)

(*) Notice: Subject to any disclaimer, the term of this patent is extended or adjusted under 35 U.S.C. 154(b) by 328 days.

(21) Appl. No.: 16/796,422

(22) Filed: Feb. 20, 2020

(65) Prior Publication Data

US 2020/0222399 A1    Jul. 16, 2020

Related U.S. Application Data

(63) Continuation of application No. 15/557,832, filed as application No. PCT/EP2016/055735 on Mar. 16, 2016, now Pat. No. 10,624,890.

(30) Foreign Application Priority Data

Mar. 16, 2015  (EP) ..................................... 15159296
Nov. 6, 2015   (EP) ..................................... 15193513

(51) Int. Cl.
| | |
|---|---|
| *A61K 31/4985* | (2006.01) |
| *A61K 31/4725* | (2006.01) |
| *A61K 31/495* | (2006.01) |
| *A61K 31/472* | (2006.01) |
| *A61P 3/04* | (2006.01) |

(52) U.S. Cl.
CPC ........ *A61K 31/4985* (2013.01); *A61K 31/472* (2013.01); *A61K 31/4725* (2013.01); *A61K 31/495* (2013.01); *A61P 3/04* (2018.01)

(58) Field of Classification Search
None
See application file for complete search history.

(56) References Cited

U.S. PATENT DOCUMENTS

| | | |
|---|---|---|
| 8,420,667 B2 | 4/2013 | Khanzhin et al. |
| 8,871,761 B2 | 10/2014 | Hoveyda et al. |
| 9,422,299 B2 | 8/2016 | Hoveyda et al. |
| 9,475,814 B2 | 10/2016 | Hoveyda et al. |
| 9,969,745 B2 | 5/2018 | Hoveyda et al. |
| 9,987,274 B2 | 6/2018 | Hoveyda et al. |
| 2014/0371218 A1 | 12/2014 | Hoveyda et al. |
| 2015/0315199 A1 | 11/2015 | Hoveyda et al. |
| 2016/0289233 A1 | 10/2016 | Hoveyda et al. |
| 2016/0304521 A1 | 10/2016 | Hoveyda et al. |
| 2016/0318941 A1 | 11/2016 | Hoveyda et al. |
| 2017/0029429 A1 | 2/2017 | Hoveyda et al. |

(Continued)

FOREIGN PATENT DOCUMENTS

| | | |
|---|---|---|
| WO | 2009/130240 A1 | 10/2009 |
| WO | 2011/121137 A1 | 10/2011 |

(Continued)

OTHER PUBLICATIONS

Must et al., "The Disease Burden Associated With Overweight and Obesity", JAMA, Oct. 1999, pp. 1523-1529, vol. 282, No. 16.

(Continued)

*Primary Examiner* — Karl J Puttlitz
(74) *Attorney, Agent, or Firm* — McCarter & English, LLP; Maria Laccotripe Zacharakis; Xin Zhang

(57) ABSTRACT

Disclosed is use of NK3R antagonists for the therapeutic treatment leptin-related disease.

8 Claims, 3 Drawing Sheets

(56) References Cited

U.S. PATENT DOCUMENTS

2017/0095472 A1 4/2017 Hoveyda et al.
2017/0298070 A1 10/2017 Hoveyda et al.

FOREIGN PATENT DOCUMENTS

| WO | 2013/050424 A1 | 4/2013 |
| WO | 2014/154895 A1 | 10/2014 |
| WO | 2014/154896 A1 | 10/2014 |
| WO | 2014/154897 A1 | 10/2014 |

OTHER PUBLICATIONS

Ozono et al., "The Efficacy and Safety of Degarelix, a GnRH Antagonist: A 12-month, Multicentre, Randomized, Maintenance Dose-finding Phase II Study in Japanese Patients with Prostate Cancer", Japanese Journal of Clinical Oncology, Mar. 2012, pp. 477-484, vol. 42, No. 6.

Tascilar et al., "The effect of gonadotropin-releasing hormone analog treatment (leuprolide) on body fat distribution in idiopathic central precocious puberty", The Turkish Journal of Pediatrics, Jan. 2011, pp. 27-33, vol. 53, No. 1.

Tolson et al., "Impaired kisspeptin signaling decreases metabolism and promotes glucose intolerance and obesity", The Journal of Clinical Investigation, Jun. 2014, vol. 124, No. 7, (5 pages).

Siuciak et al., "Disruption of the neurokinin-3 receptor (NK3) in mice leads to cognitive deficits", Psychopharmacology, Jun. 2007, pp. 185-195, vol. 194.

Li et al., "Neurokinin B Receptor Antagonism Decreases Luteinising Hormone Pulse Frequency and Amplitude and Delays Puberty Onset in the Female Rat", Journal of Neuroendocrinology, 2014, pp. 521-527, vol. 26, No. 8.

European Search Report dated May 26, 2015; from corresponding EP application No. 15 15 9296.

Karagiannides et al., "Substance P as a Novel Anti-obesity Target", Gastroenterology, Mar. 2008, pp. 747-755, vol. 134, No. 3.

Ramalho et al., "Substance P antagonist improves both obesity and asthma in a mouse model", Allergy, 2013, pp. 18-54, vol. 68.

International Search Report, dated May 27, 2016, from corresponding PCT application No. PCT/EP2016/055735.

Karagiannides et al., "Substance P (SP)-Neurokinin-1 Receptor (NK-1R) Alters Adipose Tissue Responses to High-Fat Diet and Insulin Action", Endocrinology, Jun. 2011, pp. 2197-2205, vol. 152, No. 6.

Hoveyda et al., "Discovery and Optiomization of Novel Antagonists to the Human Neurokinin-3 Receptor for the Treatment of Sex-Hormone Disorders (Part I)", Journal of Medicinal Chemistry, 2015, pp. 3060-3082, vol. 58, No. 7.

Hoveyda et al., "Optimization of Novel Antagonists to the Neurokinin-3 Receptor for the Treatment of Sex-Hormone Disorders (Part II)", Acs Medicinal Chemistry Letters, 2015, pp. 736-740, vol. 6, No. 7.

Calle et al., "Body-mass index and mortality in a prospective cohort of U.S. adults", The New England Journal of Medicine, Oct. 1999, pp. 1097-1105, vol. 341, No. 15.

Elliott et al., "N',2-Diphenylquinoline-4-carbohydrazide based NK3 receptor antagonists II", Bioorganic & Medicinal Chemistry Letters, Sep. 2006, pp. 5752-5756, vol. 16.

Mittelman-Smith et al., "Arcuate Kisspeptin/neurokinin B/Dynorphin (KNDγ) Neurons Mediate the Estrogen Suppression of Gonadotropin Secretion and Body Weight", Endocrinology, Jun. 2012, pp. 2800-2812, vol. 153, No. 6.

NK-3 RECEPTOR ANTAGONISTS FOR THERAPEUTIC TREATMENT OF LEPTIN-RELATED DISEASE

FIELD OF INVENTION

The present invention relates to the field of products dedicated to the treatment of excess body fat and/or of excess body weight, especially the treatment of excess body fat and/or the prevention of body fat gain. The present invention also relates to a cosmetic method for improving or slimming the figure and/or stimulating the loss of excess body weight, especially for stimulating the loss of excess body fat.

Especially, the invention relates to the use of NK-3 receptor antagonists (also referred to as NK3R antagonists) for the therapeutic or cosmetic treatment of excess body fat and/or of excess body weight, preferably for the therapeutic treatment of excess body fat and/or the prevention of body fat gain in patients. More specifically, the invention relates to the use, to decrease body fat and/or prevent fat gain, of selective NK3R antagonists or pharmacologically acceptable salts or solvates thereof, previously described in international patent applications WO 2011/121137, WO 2013/050424, WO 2014/154895, WO2014/154896 and WO2014/154897 in the name of the Applicant.

BACKGROUND OF INVENTION

Weight gain is a growing problem in the world population, especially in North America and Europe. Excess body weight, particularly in abdominal fat, is associated with a number of comorbidities including a significantly elevated risk for type 2 diabetes, coronary heart disease, stroke, hypertension, various types of cancer and numerous other major illnesses, and overall mortality from all causes (Must et al, 1999, JAMA 282:1523-1529, Calle et al, 1999, N. Engl. J. Med. 341:1097-1 105).

Existing therapies for the treatment and/or prevention of weight gain include for example GLP-1 agonists and central neurotransmitter modulators such as Contrave or Lorcaserin. However, these medicines generally elicit modest weight loss (3-8% after one year of treatment) and are associated with safety concerns including pancreatitis and cardiovascular effects (GLP-1 agonists) and changes in mood and/or cognition for the neurotransmitter modulators.

Non-medicinal therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and gastric bypass surgery. However, these non-medicinal therapies, although widely used are not very effective. Adherence to energy restriction diets is problematic and generally unsuccessful and the efficacy of gastric bypass surgery tends to wane over time with regard to long-term weight management.

The development of novel medicines for the treatment of excess body weight have often been limited by toxicity and side effects including tachycardia (increased heart rate), pulmonary hypertension, heart valve damage, and drug dependency (addiction).

Therefore, there remains a need for new products useful for treating and/or preventing excess body fat and/or of excess body weight.

Localized fat accumulations may also occur in a non-pathological manner (i.e. non-associated with an increased burden of disease) in individuals being in good health with a normal corpulence, according to the WHO standards. Such fat accumulation, although not directly affecting the health, may be considered as being unaesthetic. Therefore, it is also useful to develop cosmetic methods to allow people who are in good health to stabilize weight and to stay thin without localized fat deposits.

Such therapeutic or cosmetic strategies will be all the more useful as they will make it possible to preferably target body fat loss while preserving the lean body mass.

Surprisingly, the Applicant have found that the selective antagonism of the neurokinin-3 receptor (NK3R), is beneficial in weight control, specifically with regard to a reduction in body fat. The NK3 receptor is a target known to modulate the hypothalamic-pituitary-gonadal axis (HPG axis), which is of relevance to body metabolism. The Applicant also evidenced that the use of NK3R antagonists increases circulating leptin levels, which may explain the observed effect on weight and body fat. Indeed, leptin is known to be the "satiety hormone" which enables to achieve energy homeostasis and which able to trigger impressive weight loss in some patient.

The present invention is all the more surprising that inhibition or negative modulation of other targets known to modulate the HPG axis similarly to NK3 receptor is conversely reported to lead to an increase in weight gain. This was especially shown for the GnRH receptor (Ozono et al., 2012, Jpn J Clin Oncol 42:477-84; Tascilar et al., 2011, Turk J Pediatrics) and for the Kisspeptin (GPR54) receptor (Tolson et al., 2014; J Clin Invest 124:3075-3079).

Besides, a study showed that NK3-knockout mice underwent weight increase (Siociak et al., Psychopharmacology, 2007, 197, 185-195). This result is not contradictory with the findings of the present invention since the genetic deletion of the NK3 receptor cannot be assimilated to the pharmacological inhibition of a receptor activity by an NK3R antagonist, since genetic deletion of a receptor induces a lot of other changes.

Another study was conducted on rats fed with a standard chow diet or fed with a high-fat diet to which SB222200 NK3R antagonist was administered (Li et al., J. Neuroendocrinology, 2014, 26, 521-527). In this study, no effect on weight was observed. SB222200 NK3R antagonist is known to have a non-optimal pharmacological profile, which, may explain the absence of effects on weight observed in rats for SB222200.

Moreover, the present invention is all the more surprising that despite the previous drug development and clinical testing of various NK3R antagonists, it was never previously disclosed that NK3R antagonists may be beneficial in weight control, specifically with regards of reduction of body fat and so prevention of body fat gain.

The current invention demonstrates for the first time that the use of an NK3R antagonist prevents adiposity-induced weight gain. It is also evidenced that the use of an NK3R antagonist enables weight loss by reduction of fat mass, without substantial muscle loss.

SUMMARY

This invention thus relates to a NK-3 receptor antagonist for use in the therapeutic treatment of excess body weight and/or excess body fat. Especially, the invention relates to a NK-3 receptor antagonist for use in the therapeutic treatment of excess body fat or in the prevention of body fat gain in patients; provided that the NK-3 receptor antagonist is not 3-Methyl-2-phenyl-N-[(1S)-1-phenylpropyl]-4-quinolinecarboxamide.

According to one embodiment, the NK-3 receptor antagonist is selected from the group consisting of:
(a) 3-Methyl-2-phenyl-N-[(1S)-1-phenylpropyl]-4-quinolinecarboxamide
(b) (R)—N-(1-(3-(1-benzoyl-3-(3,4-dichlorophenyl)piperidin-3-yl)propyl)-4-phenyl piperidin-4-yl)-N-methylacetamide
(c) (R)-[[2-Phenyl-4-quinolinyl)carbonyl]amino]-methyl ester benzeneacetic acid
(d) N1-[1-3-[R3R)-1-Benzoyl-3-(3-(3,4-dichlorophenyl)-3-piperidinyl]propyl]-4-phenyl-piperidinyl]-N,N-dimethylurea hydrochloride
(e) 3-methanesulfonamido-2-phenyl-N-[(1S)-1-phenylpropyl]quinoline-4-carboxamide
(f) 3-Hydroxy-2-phenyl-N-[(1S)-1-phenylpropyl]-4-quinolinecarboxamide
(g) methyl 2-(3-((4-(tert-butyl)piperazin-1-yl)methyl)-8-fluoro-2-phenylquinoline-4-carbonyl)-1-phenylhydrazinecarboxylate
(h) compounds of general formula A:

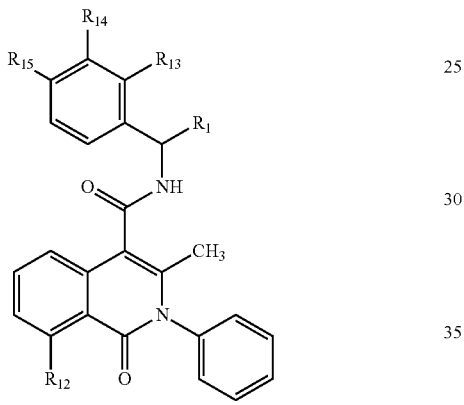

wherein $R_1$ represents ethyl, cylopropyl or cyclobutyl; wherein $R_{12}$ represents fluoro or chloro; and $R_{13}$, $R_{14}$ and $R_{15}$ each individually represent hydrogen, fluoro or chloro,
wherein two of $R_{13}$, $R_{14}$ and $R_{15}$ represent hydrogen;
(i) compounds of general formula I:

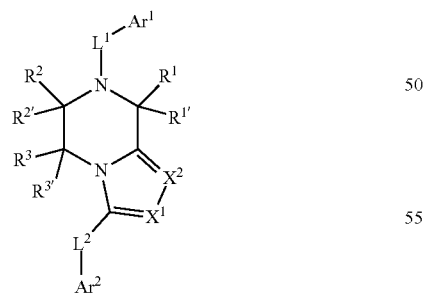

wherein
$Ar^1$ is a 5- to 6-membered aryl or heteroaryl group, 3- to 6-membered cycloalkyl group a 3- to 6-membered heterocyclyl group or a C3-C6 alkyl group, each of the aryl, heteroaryl, cycloalkyl or heterocyclyl groups being optionally substituted by one or more group(s) selected from halo, cyano, alkyl, haloalkyl, cyclopropyl, heterocyclyl, aryl, aralkyl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more aryl moiety, each of said substituents being optionally substituted by one or more further substituent(s) selected from halo, cyano, alkyl, haloalkyl, cyclopropyl, alkoxy, haloalkoxy, heterocyclyl, aryl, heteroaryl, aryloxy or heteroaryloxy;

$L^1$ is $C_1$-$C_2$ alkylene optionally being substituted by one or more group(s) selected from halo, methyl or ethyl under the condition that $R^{2'}$ together with $R^2$ form an oxo substituent, or $L^1$ is carbonyl or sulfonyl, or $L^1$ is —(C=O)—CH$_2$— where the C=O is linked to the piperazine nitrogen and the CH$_2$ to $Ar^1$;

$R^1$ is H, a $C_1$-$C_4$ alkyl, aryl or aralkyl group, each of said alkyl, aryl or aralkyl groups being optionally substituted by one or more group(s) selected from halo or hydroxyl;

$R^{1'}$ is H or a $C_1$-$C_4$ alkyl group;

$R^2$ is H or a $C_1$-$C_4$ alkyl group;

$R^{2'}$ is H or a $C_1$-$C_4$ alkyl group, or, when $L^1$ is $C_1$-$C_2$ alkylene optionally being substituted by one or more group(s) selected from halo, methyl or ethyl, $R^{2'}$ together with $R^2$ form an oxo substituent;

$R^3$ is H or a $C_1$-$C_4$ alkyl group optionally substituted by one hydroxy;

$R^{3'}$ is H or a $C_1$-$C_4$ alkyl group;

$X^1$ and $X^2$ are independently selected from N or C—Z wherein Z is H or $C_1$-$C_2$ alkyl under the condition that $X^1$ and $X^2$ cannot be both C—Z;

$L^2$ is a single bond or carbonyl;

$Ar^e$ is a 5- to 6-membered aryl or heteroaryl group, each of the aryl, or heteroaryl groups being optionally substituted by one or more group(s) selected from halo, cyano, alkyl, hydroxyalkyl, haloalkyl, cycloalkyl, heterocyclyl, aryl, heteroaryl, aralkyl, heteroarylalkyl, hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, arylsulfonylalkyl, sulfamoyl, alkylsulfamoyl, alkylsulfonylamino, haloalkylsulfonylamino, or two substituents form an alkylenedioxy group or a haloalkylenedioxy group, or fused to the aryl or heteroaryl group may be one or more cycloalkyl, aryl, heterocyclyl or heteroaryl moiety, each of said substituents being optionally substituted by one or more further substituent(s) selected from halo, cyano, alkyl, haloalkyl, alkoxy, haloalkoxy, cycloalkyl, heterocyclyl optionally substituted by alkyl, aryl, heteroaryl, hydroxyl, alkoxyalkyl, hydroxyalkoxy, alkylamino, alkylsulfonylamino, alkoxycarbonylamino, aminoalkoxy, or alkoxycarbonylaminoalkoxy;

and stereoisomers, mixture of stereoisomers, prodrugs, pharmaceutically acceptable salts, hydrates, solvates, acid salt hydrates, N-oxides and isomorphic crystalline forms thereof.

According to one embodiment, the NK-3 receptor antagonist is selected from the group consisting of (b), (c), (d), (e), (f), (g), (h) and (i) as defined above.

According to one embodiment, the NK-3 receptor antagonist is of formula I as defined above, and pharmaceutically acceptable salts and solvates thereof.

According to one embodiment, the NK-3 receptor antagonist is of formula III

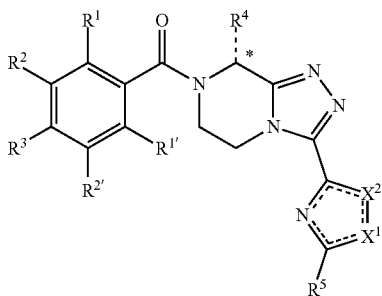

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl, nitrile or $R^3$ is thiophen-2-yl under the condition that $R^5$ is not methyl;
$R^4$ is methyl, ethyl, n-propyl, hydroxyethyl, methoxyethyl, trifluoromethyl, difluoromethyl or fluoromethyl;
$R^5$ is methyl, ethyl, methoxymethyl, trifluoromethyl, difluoromethyl, fluoromethyl, 1-fluoroethyl, 1,1-difluoroethyl or 2,2-trifluoroethyl, preferably
$R^5$ is methyl, ethyl, methoxymethyl, trifluoromethyl, difluoromethyl or fluoromethyl;
$X^1$ is N and $X^2$ is S or O; or $X^1$ is S and $X^2$ is N;
$===$ represents a single or a double bound depending on $X^1$ and $X^2$;
$^{*---}$ stands for the (R)-enantiomer or for the racemate of compound of formula III.

According to one embodiment, the NK-3 receptor antagonist for use according to the invention is under the form of a pharmaceutical composition comprising the NK-3 receptor antagonist and at least one pharmaceutically acceptable vehicle.

According to one embodiment, the NK-3 receptor antagonist is for the treatment of patients suffering from pathological excess of body fat and/or of excess body weight. According to one embodiment, the NK-3 receptor antagonist is for the treatment of patients suffering from pathological excess of body fat or for the prevention of body fat gain in patients prone to suffer from pathological excess body fat.

According to one embodiment, patients suffering from pathological excess of body fat and/or of excess body weight are selected from individuals suffering from hormonal imbalance; individuals suffering from genetic susceptibility to excess body weight; and individuals where an adipose-specific decrease in weight is deemed to be of therapeutic benefit. According to one embodiment, patients suffering from pathological excess of body fat or patients prone to suffer from pathological excess body fat are selected from individuals suffering from hormonal imbalance; individuals suffering from genetic susceptibility to excess body weight; and individuals where an adipose-specific decrease in weight is deemed to be of therapeutic benefit.

According to one embodiment, individuals suffering from hormonal imbalance are selected from women subjected to estrogen-lowering therapies; and women experiencing natural, age-related decreases in estrogen.

According to one embodiment, individuals suffering from hormonal imbalance are selected from women that undergo changes in ovarian hormone levels.

According to one embodiment, individuals suffering from hormonal imbalance are selected from men subjected to androgen-lowering therapies; and men experiencing natural, age-related decreases in circulating testosterone.

According to one embodiment, individuals where an adipose-specific decrease in weight is deemed to be of therapeutic benefit are selected from overweight individuals; individuals receiving medical treatments that are accompanied with weight gain comprising but not limited to hormonal treatment as well as steroids, pain or antipsychotic medications; individuals having inappropriate eating behaviors.

According to one embodiment, patients are leptin-sensitive patients, preferably leptin sensitive women patients.

The invention also relates to a NK-3 receptor antagonist for use in the treatment of a leptin-related disease.

According to one embodiment, the leptin-related disease is selected from metabolic disorders such as diabetes, cardiovascular diseases or metabolic syndrome; lipid regulation disorders such as lipodystrophy, including congenital and acquired lipodystrophy, dyslipidemia, nonalcoholic fatty liver disease, nonalcoholic steatohepatitis or hyperlipidemia; Congenital Leptin Deficiency; hypothalamic amenorrhea, including exercise-induced hypothalamic amenorrhea, Rabson-Mendenhall syndrome; and osteoporosis.

According to one embodiment, the NK-3 receptor antagonist for use in the treatment of a leptin-related disease is selected from the group consisting of (b), (c), (d), (e), (f), (g), (h) and (i) as defined above.

According to one embodiment, in the treatment of leptin-related diseases, the NK-3 receptor antagonist is of formula I as defined above, and pharmaceutically acceptable salts and solvates thereof. According to one embodiment, in the treatment of leptin-related diseases, the NK-3 receptor antagonist is of formula III, as defined above. According to a specific embodiment, in the treatment of leptin-related diseases, the NK-3 receptor antagonist is k-5.

The invention also relates to a cosmetic treatment method for improving the bodily appearance by stimulating the loss of body weight and/or of body fat in a subject, comprising the administration to said subject of a NK-3 receptor antagonist, and optionally the renewal of said administration until the expected cosmetic effect is obtained. Especially, the invention relates to a cosmetic treatment method for improving the bodily appearance by stimulating the loss of body weight and/or of body fat in a subject, comprising the administration to said subject of a NK-3 receptor antagonist, and optionally the renewal of said administration until the expected cosmetic effect is obtained, provided that the NK-3 receptor antagonist is not 3-Methyl-2-phenyl-N-[(1S)-1-phenylpropyl]-4-quinolinecarboxamide.

According to one embodiment, in the cosmetic treatment method of the invention, the subject is an individual being in good health and having a BMI from 18.5 to 25 kg/m².

According to one embodiment, in the cosmetic treatment method of the invention, the NK-3 receptor antagonist is selected from the group consisting of:
- (a) 3-Methyl-2-phenyl-N-[(1S)-1-phenylpropyl]-4-quinolinecarboxamide
- (b) (R)—N-(1-(3-(1-benzoyl-3-(3,4-dichlorophenyl)piperidin-3-yl)propyl)-4-phenyl piperidin-4-yl)-N-methylacetamide
- (c) (R)-[[2-Phenyl-4-quinolinyl)carbonyl]amino]-methyl ester benzeneacetic acid
- (d) N1-[1-3-[(3R)-1-Benzoyl-3-(3,4-dichlorophenyl)-3-piperidinyl]propyl]-4-phenyl-piperidinyl]-N,N-dimethylurea hydrochloride
- (e) 3-methanesulfonamido-2-phenyl-N-[(1S)-1-phenylpropyl]quinoline-4-carboxamide
- (f) 3-Hydroxy-2-phenyl-N-[(1S)-1-phenylpropyl]-4-quinolinecarboxamide
- (g) methyl 2-(3-((4-(tert-butyl)piperazin-1-yl)methyl)-8-fluoro-2-phenylquinoline-4-carbonyl)-1-phenylhydrazinecarboxylate
- (h) compounds of general formula A, as defined above
- (i) compounds of general formula I, as defined above;

and stereoisomers, mixture of stereoisomers, prodrugs, pharmaceutically acceptable salts, hydrates, solvates, acid salt hydrates, N-oxides and isomorphic crystalline forms thereof.

According to one embodiment, in the cosmetic treatment method of the invention, the NK-3 receptor antagonist is selected from the group consisting of (b), (c), (d), (e), (f), (g), (h) and (i) as defined above.

According to one embodiment, in the cosmetic treatment method of the invention, the NK-3 receptor antagonist is of formula I as defined above, and pharmaceutically acceptable salts and solvates thereof.

According to one embodiment, in the cosmetic treatment method of the invention, the NK-3 receptor antagonist is of formula III, as defined above.

Definitions

The definitions and explanations below are for the terms as used throughout the entire application, including both the specification and the claims.

The term "NK3R antagonist" or "NK-3 receptor antagonist" refers to a compound that can bind to a neurokinin B receptor (NK3R) but has little or no functional activity of its own at the receptor—thus disrupting, blocking or otherwise interfering with the action of the naturally occurring, endogenous ligand (i.e., NKB). Preferably the NK3R antagonist is a compound which competitively or non-competitively binds to the NK3R at the same site as an agonist (for example, the endogenous ligand), but does not activate an intracellular response initiated by an active form of the receptor. An antagonist thereby inhibits the intracellular response induced by an agonist.

When describing the NK3R antagonists, the terms used are to be construed in accordance with the following definitions, unless indicated otherwise.

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "halo" or "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein.

Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, propyl, n-butyl, i-butyl, s-butyl and t-butyl. $C_{x-y}$-alkyl and Cx-Cy-alkyl refer to alkyl groups which comprise from x to y carbon atoms.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "haloalkyl" alone or in combination, refers to an alkyl radical having the meaning as defined above wherein one or more hydrogens are replaced with a halogen as defined above. Examples of such haloalkyl radicals include chloromethyl, 1-bromoethyl, fluoromethyl, difluoromethyl, trifluoromethyl, 1,1,1-trifluoroethyl and the like. $C_{x-y}$-haloalkyl and Cx-Cy-alkyl refer to alkyl groups which comprise from x to y carbon atoms. Preferred haloalkyl groups are difluoromethyl, trifluoromethyl.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

When the suffix "ene" is used in conjunction with a cyclic group, this is intended to mean the cyclic group as defined herein having two single bonds as points of attachment to other groups. Therefore, "cycloalkylene" herein refers to a saturated homocyclic hydrocarbyl biradical of Formula $C_nH_{2n-2}$. Suitable cycloalkylene groups are $C_{3-6}$ cycloalkylene group, preferably a $C_{3-5}$ cycloalkylene (i.e. 1,2-cyclopropylene, 1,1-cyclopropylene, 1,1-cyclobutylene, 1,2-cyclobutylene, 1,3-cyclobutylene, 1,3-cyclopentylene, or 1,1-cyclopentylene), more preferably a $C_{3-4}$ cycloalkylene (i.e. 1,2-cyclopropylene, 1,1-cyclopropylene, 1,1-cyclobutylene, 1,2-cyclobutylene).

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The ring atoms of selected heterocyclyl and heterocyclylene moieties are numbered based on scheme below:

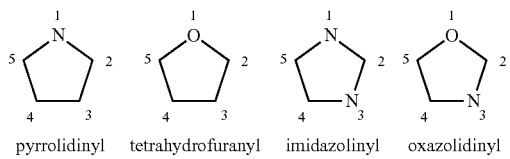

pyrrolidinyl    tetrahydrofuranyl    imidazolinyl    oxazolidinyl

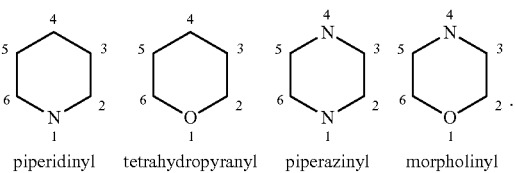

piperidinyl    tetrahydropyranyl    piperazinyl    morpholinyl

The ring atoms of fused piperazine are numbered based on scheme below

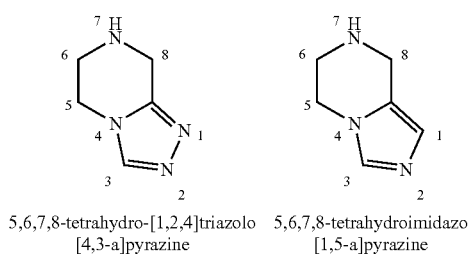

5,6,7,8-tetrahydro-[1,2,4]triazolo    5,6,7,8-tetrahydroimidazo
[4,3-a]pyrazine          [1,5-a]pyrazine -continued

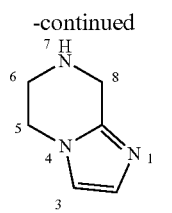

5,6,7,8-tetrahydroimidazo
[1,2-a]pyrazine

The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like. Arylene is also intended to include the partially hydrogenated derivatives of the carbocyclic systems enumerated above. Examples of such partially hydrogenated derivatives are 1,2,3,4-tetrahydronaphthylene, 1,4-dihydronaphthylene and the like.

Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "heteroarylene" as used herein means divalent carbocyclic aromatic ring systems including pyridinylene and the like.

The ring atoms of selected heteroaryl or heteroarylene moieties are numbered on scheme below:

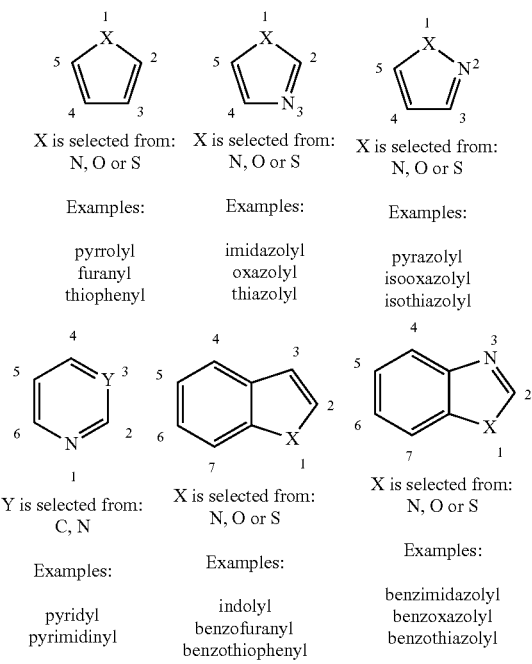

The term "carbamoyl" as used herein means a group of formula

wherein the arrow defines the attachment point.

The term "thiophen-2-yl" as used herein means a group of formula

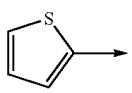

wherein the arrow defines the attachment point.

The NK3R antagonists may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art.

The bonds from an asymmetric carbon may be depicted herein using a solid line (-), a zigzag line ( ~ ), a solid wedge ( ▬ ), or a dotted wedge ( ······ ). The use of a solid line to depict bonds from an asymmetric carbon atom is meant to indicate that all possible stereoisomers in any relative ratio are meant to be included, unless it is clear from the context that a specific stereoisomer is intended. As an example, a solid line depicting bonds from an asymmetric carbon atom in a compound containing one asymmetric carbon encompasses a racemic mixture of both enantiomers. The term racemic used herein indicated a 1/1 ratio between the two enantiomers. The use of either a solid or dotted wedge to depict bonds from an asymmetric carbon atom is meant to indicate that only the stereoisomer shown is meant to be included.

The NK3R antagonists may be in the form of pharmaceutically acceptable salts. Pharmaceutically acceptable salts include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the NK3R antagonists contain an acidic group as well as a basic group the NK3R antagonists may also form internal salts, and such compounds are within the scope of the invention. When the NK3R antagonists contain a hydrogen-donating heteroatom (e.g. NH), the invention also covers salts and/or isomers formed by transfer of said hydrogen atom to a basic group or atom within the molecule.

Pharmaceutically acceptable salts of may be prepared by one or more of these methods:

(i) by reacting the compound with the desired acid;
(ii) by reacting the compound with the desired base;
(iii) by removing an acid- or base-labile protecting group from a suitable precursor of the compound or by ring-opening a suitable cyclic precursor, for example, a lactone or lactam, using the desired acid; or
(iv) by converting one salt of the compound to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of interest and one or more pharmaceutically acceptable solvent molecules, for example, ethanol. The term "hydrate" is employed when said solvent is water.

In addition, although generally, with respect to the salts of the compounds of interest, pharmaceutically acceptable salts are preferred, it should be noted that the invention in its broadest sense also included non-pharmaceutically acceptable salts, which may for example be used in the isolation and/or purification of the compounds of interest. For example, salts formed with optically active acids or bases may be used to form diastereoisomeric salts that can facilitate the separation of optically active isomers of the compounds.

The invention also generally covers all pharmaceutically acceptable predrugs and prodrugs of the NK3R antagonists.

The term "prodrug" as used herein means the pharmacologically acceptable derivatives of the compound of interest such as esters whose in vivo biotransformation product is the active drug. Prodrugs are characterized by increased bioavailability and are readily metabolized into the active compounds in vivo. Suitable prodrugs for the purpose of the invention include carboxylic esters, in particular alkyl esters, aryl esters, acyloxyalkyl esters and dioxolene carboxylic esters; ascorbic acid esters; thioesters such as alkylthio esters or aryl thioesters; and amides.

The term "predrug", as used herein, means any compound that will be modified to form a drug species, wherein the modification may take place either inside or outside of the body, and either before or after the predrug reaches the area of the body where administration of the drug is indicated.

The term "pharmaceutically acceptable" means approved or approvable by a regulatory agency or listed in recognized pharmacopeia for use in animals, and more preferably in humans. It can be material which is not biologically or otherwise undesirable, i.e. the material can be administered to an individual without causing any undesirable biological effects or interacting in a deleterious manner with any of the components of the composition in which it is contained.

The term "physiologically acceptable" refers to a medium which has no toxic or detrimental effect in the conditions of use and which is inert towards the active substance. Such a medium may for example comprise various additives depending on its purpose, such as flavors, coloring agents, fillers, preservatives, diluents, wetting agents or suspending agents, etc. Such media may also enable an immediate release, a modified release or a controlled release of one of the active substance.

The term "human" refers to subject of both genders and at any stage of development (i.e. neonate, infant, juvenile, adolescent, adult).

The term "administration", or a variant thereof (e.g., "administering"), means providing the active agent or active ingredient (e.g. a NK-3 antagonist), alone or as part of a composition, to the subject or patient in need thereof.

DETAILED DESCRIPTION

The present invention relates to the use of NK-3 receptor antagonists (also herein referred to as NK3R antagonists) for the therapeutic or cosmetic treatment of excess body fat and/or of excess body weight, preferably for the therapeutic treatment of excess body fat and/or prevention of body fat gain. Suitable NK3R antagonists and formulations thereof are described below.

NK3R Antagonists

Any suitable NK3R antagonist can be used in the therapeutic and cosmetic methods of the invention. By "suitable NK3R antagonist", it is referred to a NK3R antagonist which has a suitable pharmacological profile and especially that cross the brain barrier. Especially, any NK3R antagonist may be used, including but not limited to stereoisomers, mixture of stereoisomers, prodrugs, pharmaceutically acceptable salts, hydrates, solvates, acid salt hydrates, N-oxides and isomorphic crystalline forms thereof.

According to one embodiment, the NK3R antagonist is selected from the group comprising non-peptide small molecule antagonists including but not limited to stereoisomers, mixture of stereoisomers, prodrugs, pharmaceutically acceptable salts, hydrates, solvates, acid salt hydrates, N-oxides and isomorphic crystalline forms thereof; as well as peptide NK3R antagonists.

According to one embodiment, NK3R antagonists used in the present invention are selective NK3R antagonists. By "selective NK3R antagonist" it is referred to an antagonist of the NK3 receptor which is selective over NK1 and/or NK2 receptors.

According to one embodiment, the NK3R antagonist is selected from the group comprising (or stereoisomers, mixture of stereoisomers, prodrugs, pharmaceutically acceptable salts, hydrates, solvates, acid salt hydrates, N-oxides and isomorphic crystalline forms thereof):

(a) SB 222200 (Available from, for example, Tocris Bioscience); 3-Methyl-2-phenyl-N-[(1S)-1-phenylpropyl]-4-quinolinecarboxamide (CAS No. 174635-69-9)

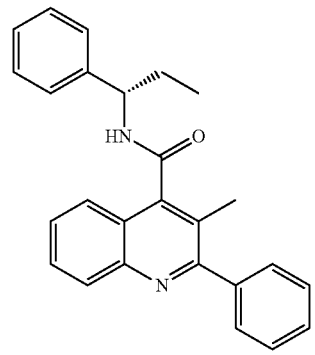 [SMILES: CC[C@H](NC(=O)c1c(C)c(-c2ccccc2)nc2ccccc12)c1ccccc1]

(b) SR 142801 (Osanetant) (Available from, for example, Axon Medchem, Germany); (R)—N-(1-(3-(1-benzoyl-3-(3,4-dichlorophenyl)piperidin-3-yl)propyl)-4-phenyl piperidin-4-yl)-N-methylacetamide (CAS No. 160492-56-8)

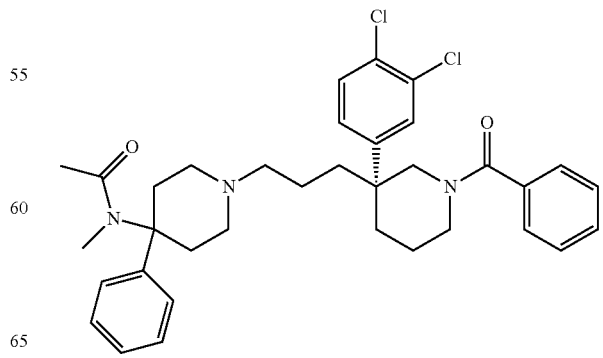

(c) SB 218795 (Available from, for example, Tocris Bioscience); (R)-[[2-Phenyl-4-quinolinyl)carbonyl]amino]-methyl ester benzeneacetic acid (CAS No. 174635-53-1)

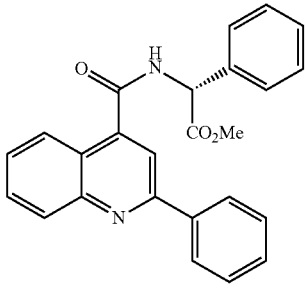 [SMILES: COC(=O)[C@H](NC(=O)c1cc(-c2ccccc2)nc2ccccc12)c1ccccc1]

(d) SSR 146977 hydrochloride (Available from, for example, Tocris Bioscience); N1-[1-3-[(3R)-1-Benzoyl-3-(3-(3,4-dichlorophenyl)-3-piperidinyl]propyl]-4-phenyl-piperidinyl]-N,N-dimethylurea hydrochloride (CAS No. 264618-38-4)

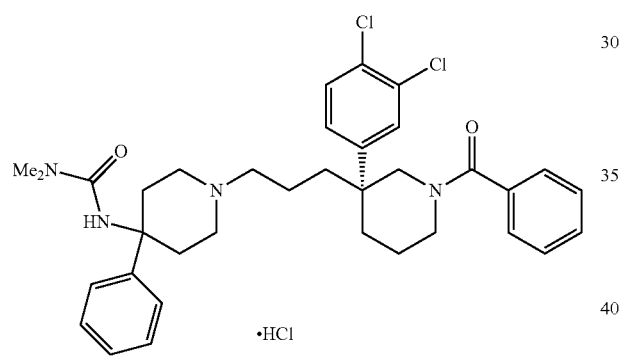

(e) AZD2624 also named AZD4901 (Astra Zeneca); 3-methanesulfonamido-2-phenyl-N-[(1S)-1-phenylpropyl] quinoline-4-carboxamide (CAS No. 941690-55-7)

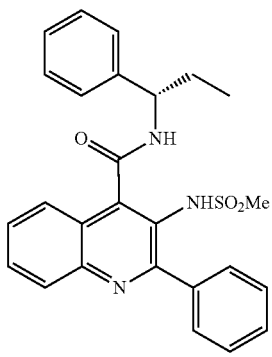

(f) SB 223412 (Talnetant) (Available from, for example, Tocris Bioscience); 3-Hydroxy-2-phenyl-N-[(1S)-1-phenyl-propyl]-4-quinolinecarboxamide (CAS No. 174636-32-9)

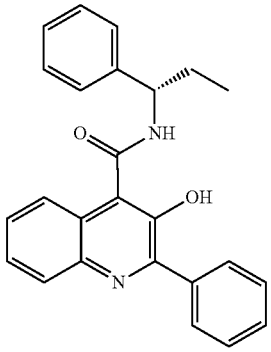 [SMILES: CC[C@H](NC(=O)c1c(O)c(-c2ccccc2)nc2ccccc12)c1ccccc1]

(g) compound 8m, disclosed in Elliott et al., Bioorg. Med. Chem. Lett., 2006, 16, 5752-5756; methyl 2-(3-((4-(tert-butyl)piperazin-1-yl)methyl)-8-fluoro-2-phenylquinoline-4-carbonyl)-1-phenylhydrazinecarboxylate

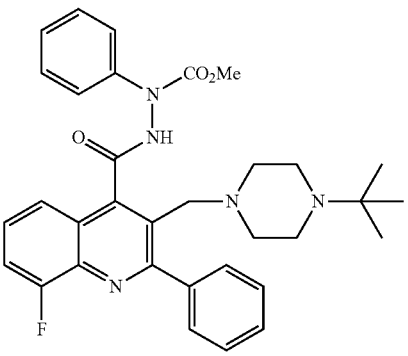 [SMILES: COC(=O)N(NC(=O)c1c(CN2CCN(C(C)(C)C)CC2)c(-c2ccccc2)nc2c(F)cccc12)c1ccccc1]

(h) one or more of the isoquinolone derivatives NK3R antagonists disclosed in U.S. Pat. No. 8,420,667, of general formula A:

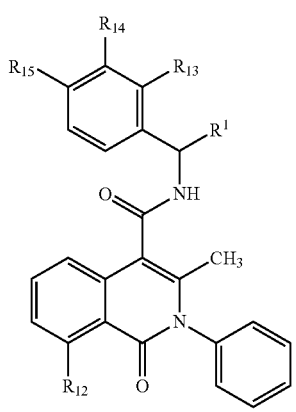

wherein $R_1$ represents ethyl, cylopropyl or cyclobutyl;
wherein $R_{12}$ represents fluoro or chloro; and
$R_{13}$, $R_{14}$ and $R_{15}$ each individually represent hydrogen, fluoro or chloro, wherein two of $R_{13}$, $R_{14}$ and $R_{15}$ represent hydrogen;
or a pharmaceutically acceptable salt thereof;

(i) one or more of the NK3R antagonists disclosed in WO 2011/121137, of general formula I:

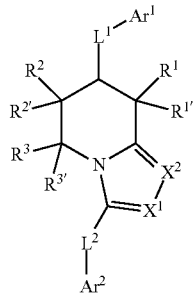

and pharmaceutically acceptable salts and solvates thereof, wherein $Ar^1$ is a 5- to 6-membered aryl or heteroaryl group, 3- to 6-membered cycloalkyl group a 3- to 6-membered heterocyclyl group or a C3-C6 alkyl group, each of the aryl, heteroaryl, cycloalkyl or heterocyclyl groups being optionally substituted by one or more group(s) selected from halo, cyano, alkyl, haloalkyl, cycloalkyl, heterocyclyl, aryl, aralkyl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more aryl moiety, each of said substituents being optionally substituted by one or more further substituent(s) selected from halo, cyano, alkyl, haloalkyl, cyclopropyl, alkoxy, haloalkoxy, heterocyclyl, aryl, heteroaryl, aryloxy or heteroaryloxy;

$L^1$ is $C_1$-$C_2$ alkylene optionally being substituted by one or more group(s) selected from halo, methyl or ethyl under the condition that $R^{2'}$ together with $R^2$ form an oxo substituent, or $L^1$ is carbonyl or sulfonyl, or $L^1$ is —(C=O)—CH$_2$— where the C=O is linked to the piperazine nitrogen and the CH$_2$ to Ar$^1$;

$R^1$ is H, a $C_1$-$C_4$ alkyl, aryl or aralkyl group, each of said alkyl, aryl or aralkyl groups being optionally substituted by one or more group(s) selected from halo or hydroxyl;

$R^{1'}$ is H or a $C_1$-$C_4$ alkyl group;
$R^2$ is H or a $C_1$-$C_4$ alkyl group;
$R^{2'}$ is H or a $C_1$-$C_4$ alkyl group, or, when $L^1$ is $C_1$-$C_2$ alkylene optionally being substituted by one or more group(s) selected from halo, methyl or ethyl, $R^{2'}$ together with $R^2$ form an oxo substituent;
$R^3$ is H or a $C_1$-$C_4$ alkyl group optionally substituted by one hydroxy;
$R^{3'}$ is H or a $C_1$-$C_4$ alkyl group;
$X^1$ and $X^2$ are independently selected from N or C—Z wherein Z is H or $C_1$-$C_2$ alkyl under the condition that $X^1$ and $X^2$ cannot be both C—Z;
$L^2$ is a single bond or carbonyl;

$Ar^2$ is a 5- to 6-membered aryl or heteroaryl group, each of the aryl, or heteroaryl groups being optionally substituted by one or more group(s) selected from halo, cyano, alkyl, hydroxyalkyl, haloalkyl, cycloalkyl, heterocyclyl, aryl, heteroaryl, aralkyl, heteroarylalkyl, hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, arylsulfonylalkyl, sulfamoyl, alkylsulfamoyl, alkylsulfonylamino, haloalkylsulfonylamino, or two substituents form an alkylenedioxy group or a haloalkylenedioxy group, or fused to the aryl or heteroaryl group may be one or more cycloalkyl, aryl, heterocyclyl or heteroaryl moiety, each of said substituents being optionally substituted by one or more further substituent(s) selected from halo, cyano, alkyl, haloalkyl, alkoxy, haloalkoxy, cycloalkyl, heterocyclyl optionally substituted by alkyl, aryl, heteroaryl, hydroxyl, alkoxyalkyl, hydroxyalkoxy, alkylamino, alkylsulfonylamino, alkoxycarbonylamino, aminoalkoxy, or alkoxycarbonylaminoalkoxy;

(j) one or more of the NK3R antagonists disclosed in WO2013/050424, of general formula II

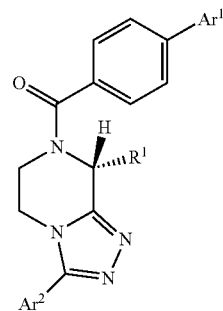

and pharmaceutically acceptable solvates thereof, wherein $Ar^1$ is unsubstituted thiophen-2-yl, unsubstituted phenyl, or 4-fluorophenyl;

$R^1$ is H or methyl;

$Ar^2$ is of general formula (i), (ii) or (iii):

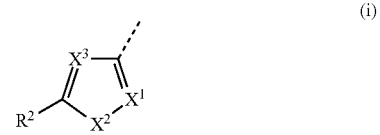

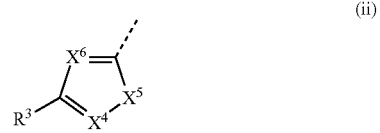

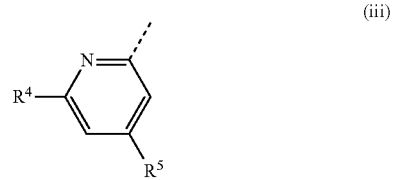

wherein
R² is linear or branched C1-C4 alkyl, C1-C2 haloalkyl, linear or branched C2-C3 alkenyl, C3-C4 cycloalkyl or di(C1-C2 alkyl)amino;

X¹ is N or C—R⁶ wherein R⁶ is H, fluoro or C1-C2 alkyl;

X² is O or S;

X³ is N, or X³ is CH under the condition that X¹ is N and X² is N—R⁷ wherein R⁷ is linear or branched C1-C3 alkyl or cyclopropyl;

R³ is linear or branched C1-C4 alkyl or C3-C4 cycloalky;

X⁴ is N or C—R⁸ wherein R⁸ is H or C1-C2 alkyl;

X⁵ is O or S;

X⁶ is N, or X⁶ is CH under the condition that X⁴ is N and X⁵ is N—R⁹ wherein R⁹ is linear or branched C1-C3 alkyl or cyclopropyl;

R⁴ is halo, cyano, methyl, or hydroxyl;

R⁵ is H or halo;

(k) one or more of the NK3R antagonists disclosed in WO2014/154895, of general formula III

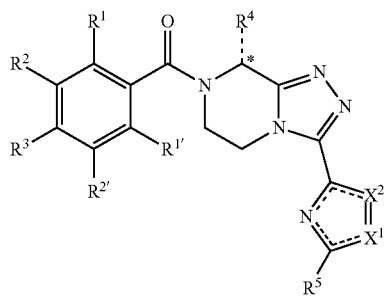

and pharmaceutically acceptable solvates thereof, wherein:

R¹ is H, F or methyl;

R¹' is H;

R² is H, F, Cl or methoxy;

R²' is H or F;

R³ is H, F, Cl, methyl, trifluoromethyl, nitrile or R³ is thiophen-2-yl under the condition that R⁵ is not methyl;

R⁴ is methyl, ethyl, n-propyl, hydroxyethyl, methoxyethyl, trifluoromethyl, difluoromethyl or fluoromethyl;

R⁵ is methyl, ethyl, methoxymethyl, trifluoromethyl, difluoromethyl, fluoromethyl, 1-fluoroethyl, 1,1-difluoroethyl or 2,2,2-trifluoroethyl, preferably R⁵ is methyl, ethyl, methoxymethyl, trifluoromethyl, difluoromethyl or fluoromethyl;

X¹ is N and X² is S or O; or X¹ is S and X² is N;

═══ represents a single or a double bound depending on X¹ and X²;

*--- stands for the (R)-enantiomer or for the racemate of compound of formula III;

(l) one or more of the NK3R antagonists disclosed in WO2014/154896;

(m) one or more of the NK3R antagonists disclosed in WO2014/154897.

According to one embodiment, compounds of formula I of group (i), as disclosed in WO2011/121137, are of formula Ib

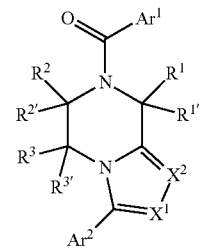

and pharmaceutically acceptable salts and solvates thereof, wherein Ar¹, Ar², R₁, R¹', R², R²', R³, R³' X¹, X², are as defined in formula I.

According to one embodiment, compounds of formula I of group (i), as disclosed in WO2011/121137, are of formula Ic

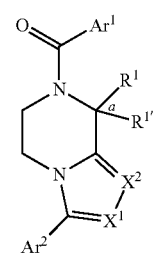

and pharmaceutically acceptable salts and solvates thereof, wherein a depicts the bond linking R1 to the piperazine moiety, and Ar¹, Ar², R¹, R¹', X¹, and X² are as defined in formula I.

According to one embodiment, compounds of formula I of group (i), as disclosed in WO2011/121137, are of formula Id-1

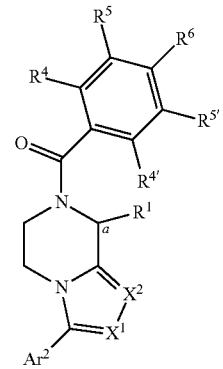

and pharmaceutically acceptable salts and solvates thereof, wherein a depicts the bond linking R¹ to the piperazine moiety; and Ar², R¹, X¹ and X² are as defined in formula I; and R⁴, R⁴', R⁵, R⁵' and R⁶ are independently selected from H, halo, cyano, alkyl, haloalkyl, C3-C6 cycloalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^5$ together with $R^4$ or $R^6$, or $R^{5'}$ together with $R^{4'}$ or $R^6$ forms an alkylenedioxy group or a haloalkylenedioxy group, or $R^5$ together with $R^4$ or $R^6$, or $R^{5'}$ together with $R^{4'}$ or $R^6$ forms an aryl moiety fused to the phenyl group to which they are attached, each of said substituents being optionally substituted by one or more further substituent(s) selected from halo, cyano, alkyl, haloalkyl, cyclopropyl.

According to one embodiment, compounds of formula I of group (i), as disclosed in WO2011/121137, are of formula Ie-1

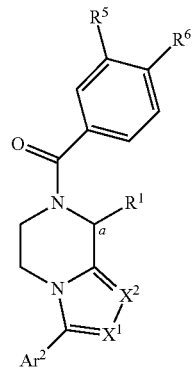

and pharmaceutically acceptable salts and solvates thereof, wherein a depicts the bond linking $R^1$ to the piperazine moiety; and $Ar^2$, $R^1$, $X^1$ and $X^2$ are as defined in formula I; and $R^5$ and $R^6$ are independently selected from H, halo, cyano, alkyl, cyclopropyl, aryl, heteroaryl, each of said aryl and heteroaryl groups being optionally substituted by one or more group(s) selected from halo, alkyl, cyclopropyl, or $R^5$ and $R^6$ together form a phenyl moiety fused to the phenyl ring they are attached to.

According to one embodiment, compounds of formula III of group (k), as disclosed in WO2014/154895, are of formula IIIa

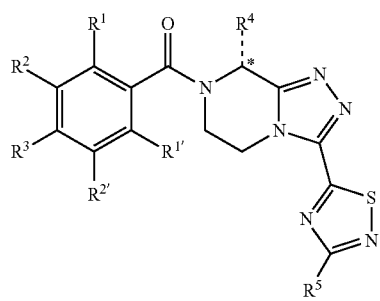

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl or nitrile;

$R^4$ is methyl, ethyl, n-propyl, hydroxyethyl, methoxyethyl, trifluoromethyl, difluoromethyl or fluoromethyl, preferably $R^4$ is methyl, ethyl, n-propyl or hydroxyethyl;
$R^5$ is methyl, ethyl, methoxymethyl, trifluoromethyl, difluoromethyl, fluoromethyl, 1-fluoroethyl, 1,1-difluoroethyl or 2,2,2-trifluoroethyl, preferably
$R^5$ is methyl, ethyl, methoxymethyl, trifluoromethyl, difluoromethyl or fluoromethyl, preferably $R^5$ is methyl, ethyl, trifluoromethyl or difluoromethyl, preferably $R^5$ is methyl, ethyl or trifluoromethyl;
$\overset{*}{\text{- - -}}$ stands for the (R)-enantiomer or for the racemate of compound of Formula Ia.

According to one embodiment, compounds of formula III of group (k), as disclosed in WO2014/154895, are of formula IIIa-1

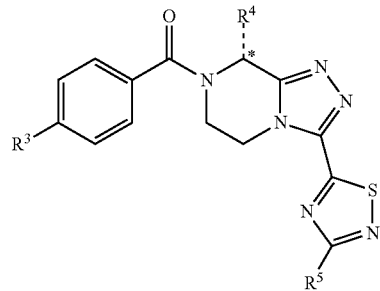

and pharmaceutically acceptable solvates thereof, wherein:
$R^3$ is H, F, Cl, methyl, trifluoromethyl or nitrile, preferably $R^3$ is H, F or Cl;
$R^4$ is methyl, ethyl, n-propyl, hydroxyethyl, methoxyethyl, trifluoromethyl, difluoromethyl or fluoromethyl, preferably $R^4$ is methyl, ethyl, n-propyl or hydroxyethyl;
$R^5$ is methyl, ethyl, methoxymethyl, trifluoromethyl, difluoromethyl, fluoromethyl, 1-fluoroethyl, 1,1-difluoroethyl or 2,2,2-trifluoroethyl, preferably
$R^5$ is methyl, ethyl, methoxymethyl, trifluoromethyl, difluoromethyl or fluoromethyl, preferably $R^5$ is methyl, ethyl, trifluoromethyl or difluoromethyl, preferably $R^5$ is methyl, ethyl or trifluoromethyl;
$\overset{*}{\text{- - -}}$ stands for the (R)-enantiomer or for the racemate.

According to one embodiment, compounds of formula III of group (k), as disclosed in WO2014/154895, are of formula IIIa-1'

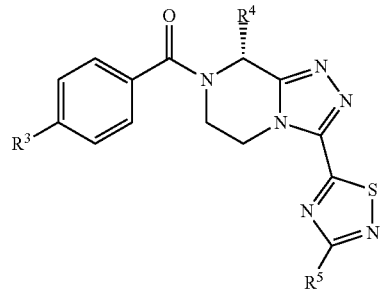

and pharmaceutically acceptable solvates thereof, wherein $R^3$, $R^4$ and $R^5$ are as defined in formula IIIa-1.

According to one embodiment, specific compounds of group (i), as disclosed in WO2011/121137, of group (j), as disclosed in WO2013/050424 and of group (k), as disclosed in WO2014/154895 include compounds below:

| Cpd n° | Structure | Chemical name | MW |
|---|---|---|---|
| i-71 | 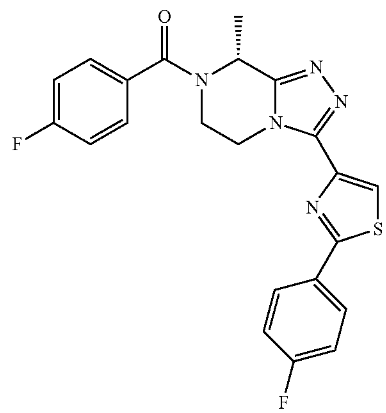 [SMILES: C[C@@H]1c2nnc(-c3csc(-c4ccc(F)cc4)n3)n2CCN1C(=O)c1ccc(F)cc1] | (R)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 438.5 |
| i-114 | 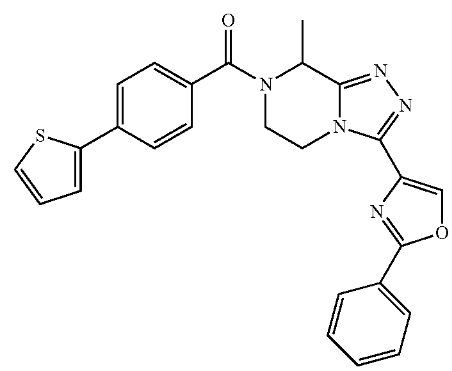 [SMILES: CC1c2nnc(-c3coc(-c4ccccc4)n3)n2CCN1C(=O)c1ccc(-c2cccs2)cc1] | (8-methyl-3-(2-phenyloxazol-4-yl)-5,6-dihydro-[1,2,4]triazolo[4,3-a]pyrazin-7(8H)-yl)(4-(thiophen-2-yl)phenyl)methanone | 468.5 |
| i-144 | 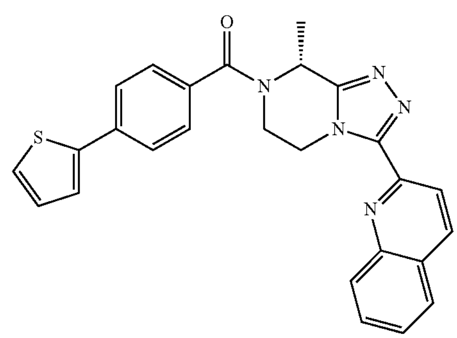 [SMILES: C[C@@H]1c2nnc(-c3ccc4ccccc4n3)n2CCN1C(=O)c1ccc(-c2cccs2)cc1] | (R)-(8-methyl-3-(quinolin-2-yl)-5,6-dihydro-[1,2,4]triazolo[4,3-a]pyrazin-7(8H)-yl)(4-(thiophen-2-yl)phenyl)methanone | 452.5 |
| i-156 | 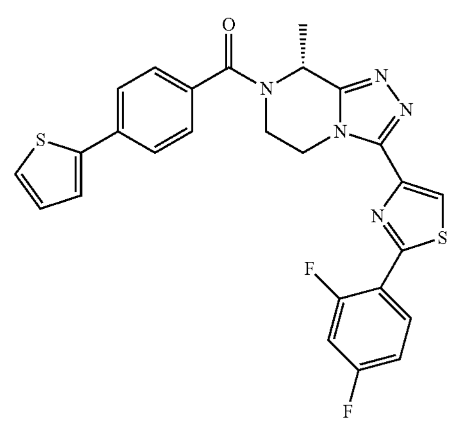 [SMILES: C[C@@H]1c2nnc(-c3csc(-c4ccc(F)cc4F)n3)n2CCN1C(=O)c1ccc(-c2cccs2)cc1] | (R)-(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 520.6 |

-continued

| Cpd n° | Structure | Chemical name | MW |
|---|---|---|---|
| j-1 | 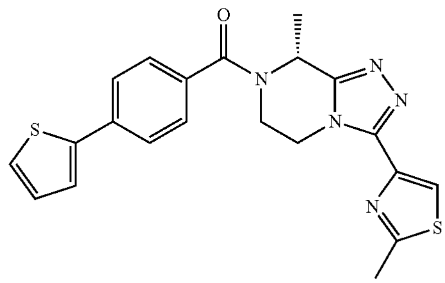 [SMILES: Cc1nc(-c2nnc3n2CCN(C(=O)c2ccc(-c4cccs4)cc2)[C@@H]3C)cs1] | (R)-(8-methyl-3-(2-methylthiazol-4-yl)-5,6-dihydro-[1,2,4]triazolo[4,3-a]pyrazin-7(8H)-yl)(4-(thiophen-2-yl)phenyl)methanone | 421.53 |
| j-19 | 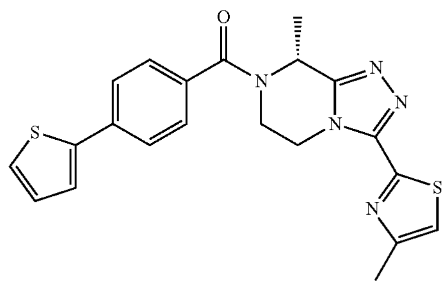 [SMILES: Cc1csc(-c2nnc3n2CCN(C(=O)c2ccc(-c4cccs4)cc2)[C@@H]3C)n1] | (R)-(8-methyl-3-(4-methylthiazol-2-yl)-5,6-dihydro-[1,2,4]triazolo[4,3-a]pyrazin-7(8H)-yl)(4-(thiophen-2-yl)phenyl)methanone | 421.54 |
| k-1 | 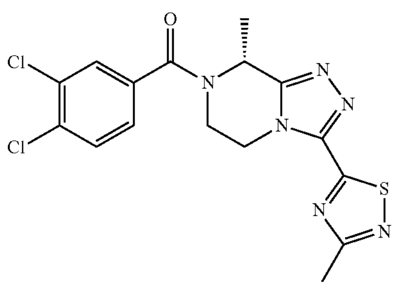 [SMILES: Cc1nsc(-c2nnc3n2CCN(C(=O)c2ccc(Cl)c(Cl)c2)[C@@H]3C)n1] | (R)-(3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone | 409.29 |
| k-2 | 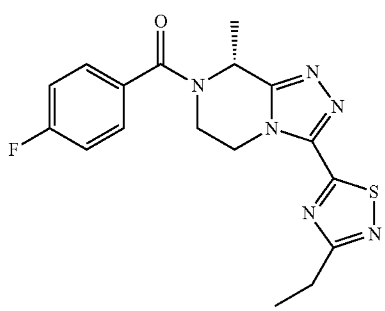 [SMILES: CCc1nsc(-c2nnc3n2CCN(C(=O)c2ccc(F)cc2)[C@@H]3C)n1] | (R)-(3-(3-ethyl-1,2,4-thiadiazol-5-yl)-8-methyl-5,6-dihydro-[1,2,4]triazolo[4,3-a]pyrazin-7(8H)-yl)(4-fluorophenyl)methanone | 372.42 |
| k-3 | 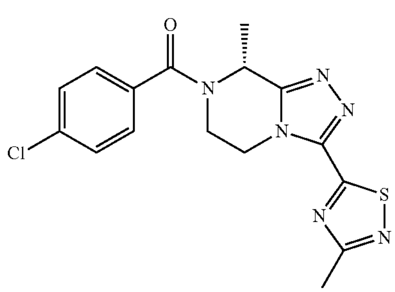 [SMILES: Cc1nsc(-c2nnc3n2CCN(C(=O)c2ccc(Cl)cc2)[C@@H]3C)n1] | (R)-(4-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |

-continued

| Cpd n° | Structure | Chemical name | MW |
|---|---|---|---|
| k-4 | 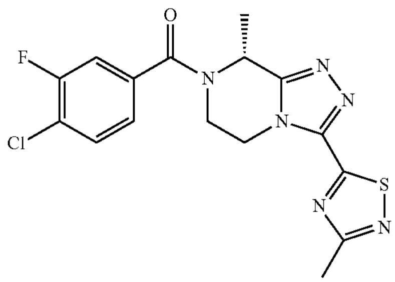 [SMILES: Cc1nsc(-c2nnc3n2CCN(C(=O)c2ccc(Cl)c(F)c2)[C@@H]3C)n1] | (R)-(4-chloro-3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| k-5 | 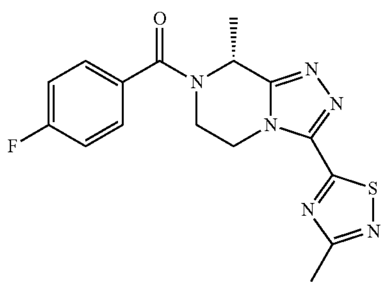 [SMILES: Cc1nsc(-c2nnc3n2CCN(C(=O)c2ccc(F)cc2)[C@@H]3C)n1] | (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| k-6 | 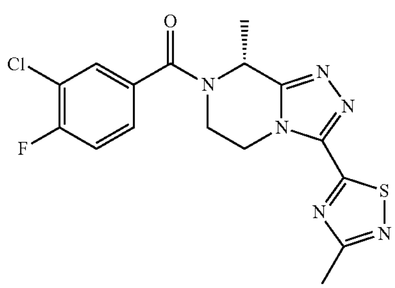 [SMILES: Cc1nsc(-c2nnc3n2CCN(C(=O)c2ccc(F)c(Cl)c2)[C@@H]3C)n1] | (R)-(3-chloro-4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| k-7 | 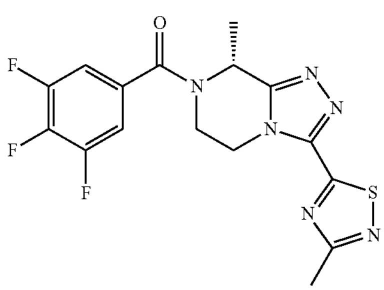 [SMILES: Cc1nsc(-c2nnc3n2CCN(C(=O)c2cc(F)c(F)c(F)c2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(3,4,5-trifluorophenyl)methanone | 394.37 |
| k-8 | 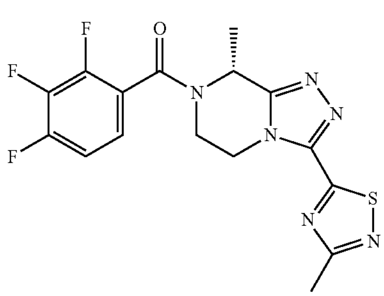 [SMILES: Cc1nsc(-c2nnc3n2CCN(C(=O)c2ccc(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4-trifluorophenyl)methanone | 394.37 |

-continued

| Cpd n° | Structure | Chemical name | MW |
|---|---|---|---|
| k-9 | 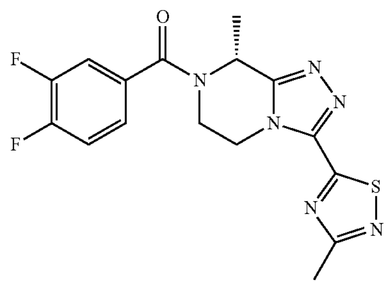 [SMILES: Cc1nsc(-c2nnc3n2CCN(C(=O)c2ccc(F)c(F)c2)[C@@H]3C)n1] | (R)-(3,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| k-10 | 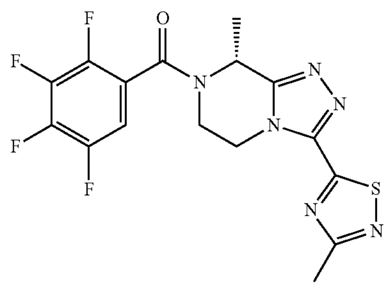 [SMILES: Cc1nsc(-c2nnc3n2CCN(C(=O)c2cc(F)c(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4,5-tetrafluorophenyl)methanone | 421.36 |
| k-11 | 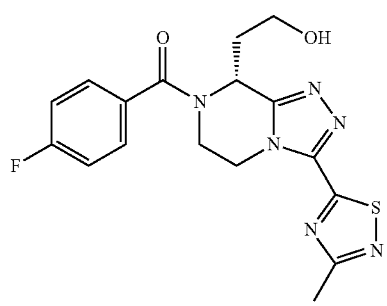 [SMILES: Cc1nsc(-c2nnc3n2CCN(C(=O)c2ccc(F)cc2)[C@@H]3CCO)n1] | (R)-(4-fluorophenyl)(8-(2-hydroxyethyl)-3-(3-methyl-1,2,4-thiadiazol-5-yl)-5,6-dihydro-[1,2,4]triazolo[4,3-a]pyrazin-7(8H)-yl)methanone | 388.42 |
| k-12 | 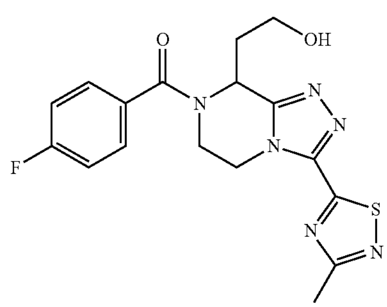 [SMILES: Cc1nsc(-c2nnc3n2CCN(C(=O)c2ccc(F)cc2)C3CCO)n1] | (4-fluorophenyl)(8-(2-hydroxyethyl)-3-(3-methyl-1,2,4-thiadiazol-5-yl)-5,6-dihydro-[1,2,4]triazolo[4,3-a]pyrazin-7(8H)-yl)methanone | 388.42 |
| k-13 | 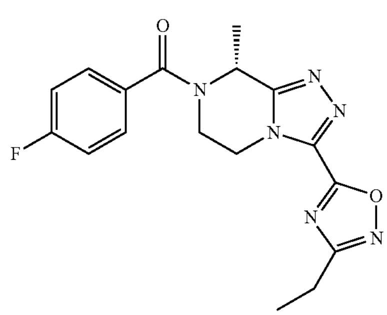 [SMILES: CCc1noc(-c2nnc3n2CCN(C(=O)c2ccc(F)cc2)[C@@H]3C)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-fluorophenyl)methanone | 356.35 |

| Cpd n° | Structure | Chemical name | MW |
|---|---|---|---|
| k-14 | 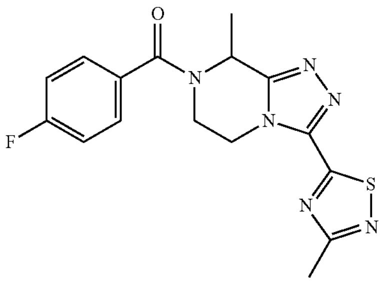 [SMILES: Cc1nsc(-c2nnc3n2CCN(C(=O)c2ccc(F)cc2)C3C)n1] | (4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| k-15 | 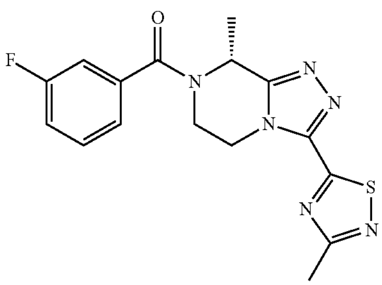 [SMILES: Cc1nsc(-c2nnc3n2CCN(C(=O)c2cccc(F)c2)[C@@H]3C)n1] | (R)-(3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| k-16 | 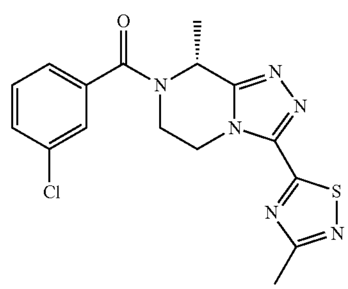 [SMILES: Cc1nsc(-c2nnc3n2CCN(C(=O)c2cccc(Cl)c2)[C@@H]3C)n1] | (R)-(3-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |
| k-17 | 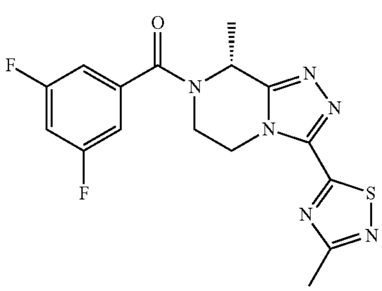 [SMILES: Cc1nsc(-c2nnc3n2CCN(C(=O)c2cc(F)cc(F)c2)[C@@H]3C)n1] | (R)-(3,5-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| k-18 | 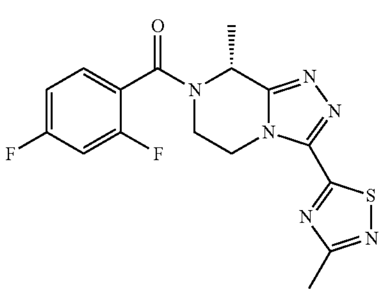 [SMILES: Cc1nsc(-c2nnc3n2CCN(C(=O)c2ccc(F)cc2F)[C@@H]3C)n1] | (R)-(2,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |

-continued

| Cpd n° | Structure | Chemical name | MW |
|---|---|---|---|
| k-19 | 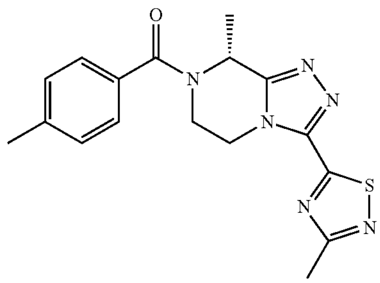 [SMILES: Cc1ccc(C(=O)N2CCn3c(-c4nc(C)ns4)nnc3[C@H]2C)cc1] | (R)-(8-methyl-3-(3-methyl-1,2,4-thiadiazol-5-yl)-5,6-dihydro-[1,2,4]triazolo[4,3-a]pyrazin-7(8H)-yl)(p-tolyl)methanone | 354.43 |
| k-20 | 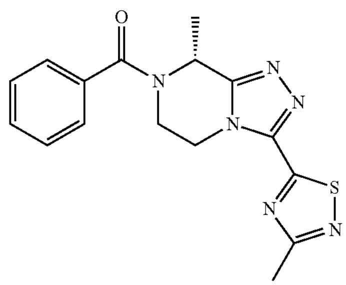 [SMILES: Cc1nsc(-c2nnc3n2CCN(C(=O)c2ccccc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(phenyl)methanone | 340.4 |
| k-21 | 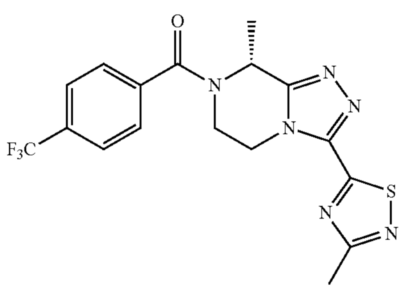 [SMILES: Cc1nsc(-c2nnc3n2CCN(C(=O)c2ccc(C(F)(F)F)cc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(4-(trifluoromethyl)phenyl)methanone | 408.4 |
| k-22 | 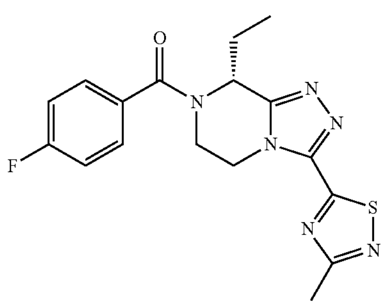 | (R)-(8-ethyl-3-(3-methyl-1,2,4-thiadiazol-5-yl)-5,6-dihydro-[1,2,4]triazolo[4,3-a]pyrazin-7(8H)-yl)(4-fluorophenyl)methanone | 372.42 |
| k-23 | 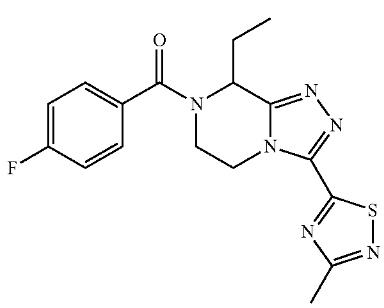 [SMILES: CCC1c2nnc(-c3nc(C)ns3)n2CCN1C(=O)c1ccc(F)cc1] | (8-ethyl-3-(3-methyl-1,2,4-thiadiazol-5-yl)-5,6-dihydro-[1,2,4]triazolo[4,3-a]pyrazin-7(8H)-yl)(4-fluorophenyl)methanone | 372.42 |

-continued

| Cpd nº | Structure | Chemical name | MW |
|---|---|---|---|
| k-24 | 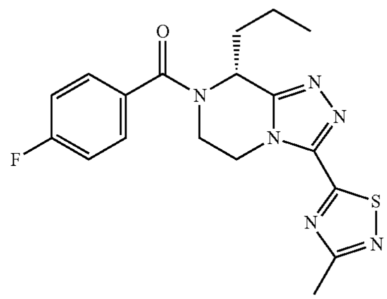 [SMILES: CCC[C@@H]1c2nnc(-c3nc(C)ns3)n2CCN1C(=O)c1ccc(F)cc1] | (R)-(4-fluorophenyl)(3-(3-methyl-1,2,4-thiadiazol-5-yl)-8-propyl-5,6-dihydro-[1,2,4]triazolo[4,3-a]pyrazin-7(8H)-yl)methanone | 386.45 |
| k-25 | 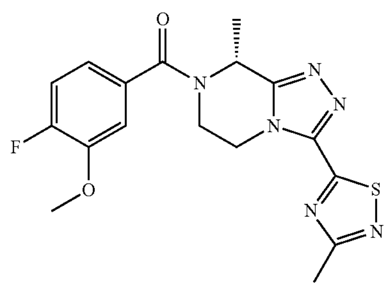 [SMILES: COc1cc(C(=O)N2CCn3c(-c4nc(C)ns4)nnc3[C@H]2C)ccc1F] | (R)-(4-fluoro-3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 388.42 |
| k-26 | 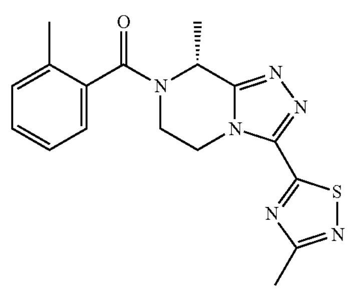 [SMILES: Cc1nsc(-c2nnc3n2CCN(C(=O)c2ccccc2C)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(o-tolyl)methanone | 354.43 |
| k-27 | 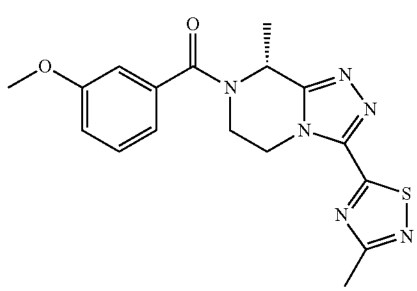 [SMILES: COc1cccc(C(=O)N2CCn3c(-c4nc(C)ns4)nnc3[C@H]2C)c1] | (R)-(3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 370.43 |
| k-28 | 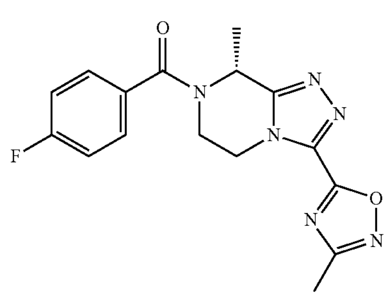 [SMILES: Cc1noc(-c2nnc3n2CCN(C(=O)c2ccc(F)cc2)[C@@H]3C)n1] | (R)-(4-fluorophenyl)(8-methyl-3-(3-methyl-1,2,4-oxadiazol-5-yl)-5,6-dihydro-[1,2,4]triazolo[4,3-a]pyrazin-7(8H)-yl)methanone | 342.33 |

| Cpd n° | Structure | Chemical name | MW |
|---|---|---|---|
| k-29 | 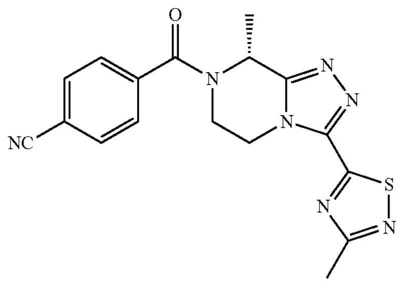 [SMILES: Cc1nsc(-c2nnc3n2CCN(C(=O)c2ccc(C#N)cc2)[C@@H]3C)n1] | (R)-4-(8-methyl-3-(3-methyl-1,2,4-thiadiazol-5-yl)-5,6,7,8-tetrahydro-[1,2,4]triazolo[4,3-a]pyrazine-7-carbonyl)benzonitrile | 365.41 |
| k-30 | 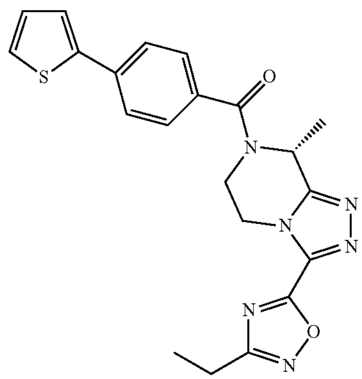 [SMILES: CCc1noc(-c2nnc3n2CCN(C(=O)c2ccc(-c4cccs4)cc2)[C@@H]3C)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 420.49 |
| k-31 | 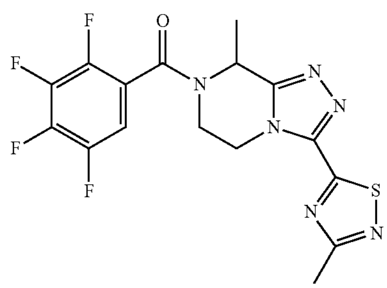 [SMILES: Cc1nsc(-c2nnc3n2CCN(C(=O)c2cc(F)c(F)c(F)c2F)C3C)n1] | (8-methyl-3-(3-methyl-1,2,4-thiadiazol-5-yl)-5,6-dihydro-[1,2,4]triazolo[4,3-a]pyrazin-7(8H)-yl)(2,3,4,5-tetrafluorophenyl)methanone | 412.36 |
| k-32 | 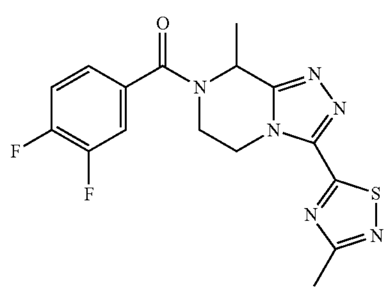 [SMILES: Cc1nsc(-c2nnc3n2CCN(C(=O)c2ccc(F)c(F)c2)C3C)n1] | (3,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| k-33 | 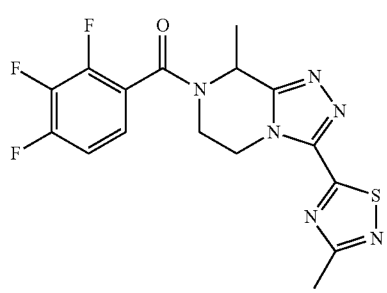 [SMILES: Cc1nsc(-c2nnc3n2CCN(C(=O)c2ccc(F)c(F)c2F)C3C)n1] | (8-methyl-3-(3-methyl-1,2,4-thiadiazol-5-yl)-5,6-dihydro-[1,2,4]triazolo[4,3-a]pyrazin-7(8H)-yl)(2,3,4-trifluorophenyl)methanone | 394.37 |

| Cpd n° | Structure | Chemical name | MW |
|---|---|---|---|
| k-34 | 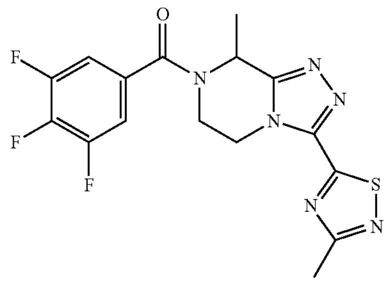 [SMILES: Cc1nsc(-c2nnc3n2CCN(C(=O)c2cc(F)c(F)c(F)c2)C3C)n1] | (8-methyl-3-(3-methyl-1,2,4-thiadiazol-5-yl)-5,6-dihydro-[1,2,4]triazolo[4,3-a]pyrazin-7(8H)-yl)(3,4,5-trifluorophenyl)methanone | 394.37 |
| k-35 | 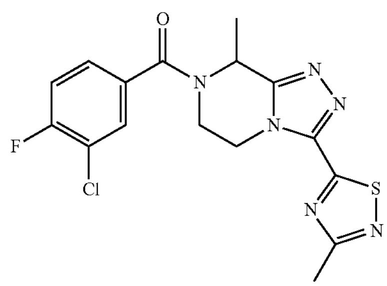 [SMILES: Cc1nsc(-c2nnc3n2CCN(C(=O)c2ccc(F)c(Cl)c2)C3C)n1] | (3-chloro-4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| k-36 | 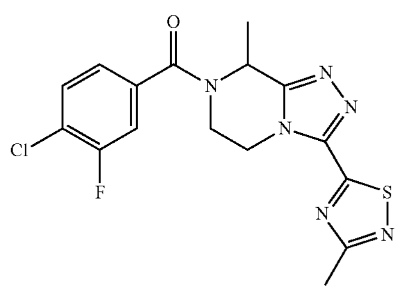 [SMILES: Cc1nsc(-c2nnc3n2CCN(C(=O)c2ccc(Cl)c(F)c2)C3C)n1] | (4-chloro-3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| k-37 | 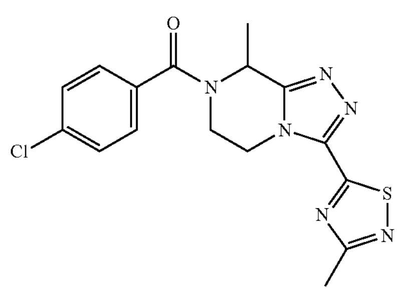 [SMILES: Cc1nsc(-c2nnc3n2CCN(C(=O)c2ccc(Cl)cc2)C3C)n1] | (4-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |
| k-38 | 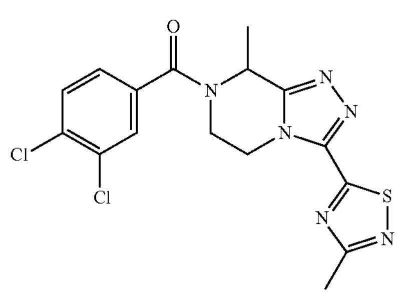 [SMILES: Cc1nsc(-c2nnc3n2CCN(C(=O)c2ccc(Cl)c(Cl)c2)C3C)n1] | (3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone | 409.29 |

-continued

| Cpd nº | Structure | Chemical name | MW |
|---|---|---|---|
| k-39 | 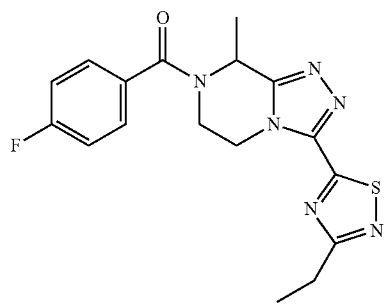 [SMILES: CCc1nsc(-c2nnc3n2CCN(C(=O)c2ccc(F)cc2)C3C)n1] | (3-(3-ethyl-1,2,4-thiadiazol-5-yl)-8-methyl-5,6-dihydro-[1,2,4]triazolo[4,3-a]pyrazin-7(8H)-yl)(4-fluorophenyl)methanone | 372.42 |
| k-40 | 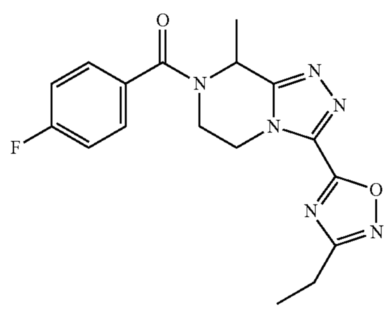 [SMILES: CCc1noc(-c2nnc3n2CCN(C(=O)c2ccc(F)cc2)C3C)n1] | (3-(3-ethyl-1,2,4-oxadiazol-5-yl)-8-methyl-5,6-dihydro-[1,2,4]triazolo[4,3-a]pyrazin-7(8H)-yl)(4-fluorophenyl)methanone | 356.35 |
| k-41 | 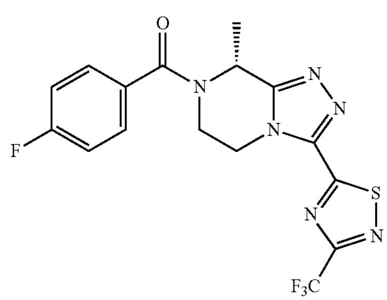 [SMILES: C[C@@H]1c2nnc(-c3nc(C(F)(F)F)ns3)n2CCN1C(=O)c1ccc(F)cc1] | (R)-(4-fluorophenyl)(8-methyl-3-(trifluoromethyl)-1,2,4-thiadiazol-5-yl)-5,6-dihydro-[1,2,4]triazolo[4,3-a]pyrazin-7(8H)-yl)methanone | 412.36 |
| k-42 | 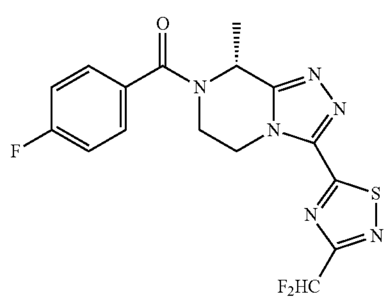 [SMILES: C[C@@H]1c2nnc(-c3nc(C(F)F)ns3)n2CCN1C(=O)c1ccc(F)cc1] | (R)-(3-(3-(difluoromethyl)-1,2,4-thiadiazol-5-yl)-8-methyl-5,6-dihydro-[1,2,4]triazolo[4,3-a]pyrazin-7(8H)-yl)(4-fluorophenyl)methanone | 394.37 |
| k-43 | 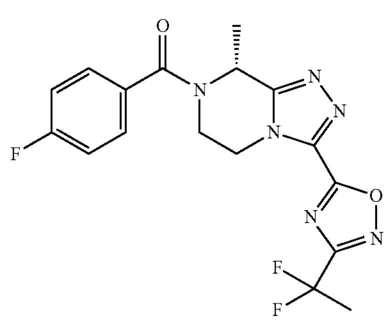 [SMILES: C[C@@H]1c2nnc(-c3nc(C(C)(F)F)no3)n2CCN1C(=O)c1ccc(F)cc1] | (R)-(3-(3-(1,1-difluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 392.34 |

-continued

| Cpd n° | Structure | Chemical name | MW |
|---|---|---|---|
| k-44 | 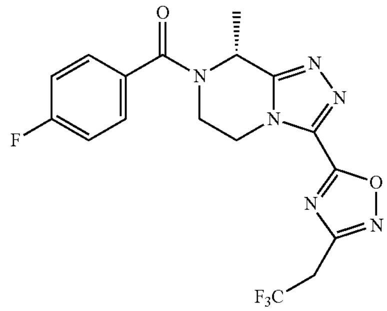 [SMILES: C[C@@H]1c2nnc(-c3nc(CC(F)(F)F)no3)n2CCN1C(=O)c1ccc(F)cc1] | (R)-(4-fluorophenyl)(8-methyl-3-(3-(2,2,2-trifluoroethyl)-1,2,4-oxadiazol-5-yl)-5,6-dihydro-[1,2,4]triazolo[4,3-a]pyrazin-7(8H)-yl)methanone | 410.33 |
| k-45 | | ((8R)-3-(3-(1-fluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 374.34 | and pharmaceutically acceptable solvates thereof.

In Table 1, the term "Cpd" means compound. The compounds were named using ChemBioDraw® Ultra version 12.0 (PerkinElmer).

According to a specific embodiment, the NK3R antagonist is k-5.

According to a specific embodiment, the NK3R antagonist is not SB 222200.

Formulations Comprising NK3R Antagonists

The present invention also relates to formulations comprising NK3R antagonists for use in the therapeutic or cosmetic treatment of excess body fat and/or of excess body weight, preferably in the therapeutic treatment of excess body fat and/or prevention of body fat gain.

In the case of the therapeutic treatment of excess body fat and/or of excess body weight, preferably in the therapeutic treatment of excess body fat and/or prevention of body fat gain, the formulation is a pharmaceutical composition. According to one embodiment, the pharmaceutical composition comprises an NK3R antagonist as described above and at least one pharmaceutically acceptable vehicle, such as for example at least one carrier, diluent, excipient and/or adjuvant. As indicated above, the NK3R antagonist may be a stereoisomer, a mixture of stereoisomers, a prodrug, a pharmaceutically acceptable salt, a hydrate, a solvate, an acid salt hydrate, an N-oxide or an isomorphic crystalline form.

In the case of the cosmetic treatment of excess body fat and/or of excess body weight, the formulation is a cosmetic composition. According to one embodiment, the cosmetic composition comprises an NK3R antagonist as described above and at least one physiologically acceptable carrier, diluent, excipient and/or adjuvant. As indicated above, the NK3R antagonist may be a stereoisomer, a mixture of stereoisomers, a prodrug, a pharmaceutically acceptable salt, a hydrate, a solvate, an acid salt hydrate, an N-oxide or an isomorphic crystalline form.

The formulation of the NK3R antagonist for use according to the present invention as well as its amount depend on the therapeutic or cosmetic purpose of the treatment, and will be clear to the skilled person.

By means of non-limiting examples, such formulations may be in a form suitable for oral administration, for parenteral administration (such as by intravenous, intramuscular or subcutaneous injection or intravenous infusion), for topical administration (including ocular), for administration by inhalation, for transdermal administration such as for example by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made for example to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in such formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

According to a specific embodiment, the formulation is in a form suitable for oral administration. According to a preferred embodiment, the formulation is under the form of tablets, pills, powders, lozenges, sachets, cachets, elixirs, suspensions, emulsions, solutions, syrups, aerosols, soft and hard gelatin capsules, or drops. According to a specific embodiment, the formulation is under the form of tablets. According to another specific embodiment, the formulation is under the form of soft or hard gelatin capsules. According to another specific embodiment, the formulation is under the form of loose powder, preferably contained in sachets.

The formulations of the invention are preferably in a unit dosage form, and may be suitably packaged, for example in a box, blister, vial, bottle, sachet, ampoule or in any other suitable single-dose or multi-dose holder or container (which may be properly labelled); optionally with one or more leaflets containing product information and/or instructions for use. Generally, such unit dosages will contain between 0.05 and 1000 mg, and usually between 1 and 500 mg, preferably between 2 and 150 mg of NK3R antagonist, e.g. about 2, 4, 8, 16, 32, 64 or 128 mg per unit dosage. According to another embodiment, such unit dosages will contain between 0.05 and 1000 mg, and usually between 1 and 500 mg, preferably between 2 and 400 mg, preferably between 2 and 200 mg of NK3R antagonist per unit dosage.

Depending on the therapeutic or cosmetic use and the route of administration, the NK3R antagonist will usually be administered between 0.001 and 10 mg per kilogram body weight, more often between 0.01 and 4 mg per kilogram body weight, preferably between 0.02 and 1.5 mg per kilogram body weight, for example about 0.02, 0.04, 0.08, 0.16, 0.32, 0.64 or 1.28 mg, per kilogram body weight of the patient per day, which may be administered as a single daily dose, divided over one or more daily doses, or essentially continuously, e.g. using a drip infusion. According to another embodiment, the NK3R antagonist will usually be administered between 0.001 and 10 mg per kilogram body weight, more often between 0.01 and 7 mg per kilogram body weight, preferably between 0.03 and 3.5 mg per kilogram body weight of the patient per day, which may be administered as a single daily dose, divided over one or more daily doses, or essentially continuously, e.g. using a drip infusion.

According to one embodiment, less than 55 mg of the NK3R antagonist is administered to the patient, preferably less than 40 mg, more preferably less than 30 mg, even more preferably less than 20 mg. According to another embodiment, more than 55 mg of the NK3R antagonist is administered to the patient, preferably from 55 to 200 mg, more preferably from 60 to 180 mg.

According to one embodiment, the NK3R antagonists for use in the therapeutic or cosmetic methods of the invention can be administered in combination with other therapeutic agents and/or active ingredients.

In one embodiment of the invention, the NK3R antagonist may be administered in combination with other additional active substances or compounds, provided said additional active substances or compounds are not detrimental to the therapeutic or cosmetic activity of the NK3R antagonist for use of the invention.

Advantageously, an additional active substance stimulates the weight loss or the body fat reduction and/or contributes to the prevention of weight gain or of body fat development.

Any additional compound with a nutritional interest and/or stimulating weight loss or body fat reduction, or preventing fat gain, may also be added to the NK3R antagonist for use of the invention in a pharmaceutical or cosmetic form. It may be for example, vitamins, mineral salts, essential amino acids, essential fatty acids, oligo-elements, various natural extracts, fibers, antioxidants, flavonoids.

In the case of combination regimen, the NK3R antagonist and other active substances may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

Uses

The present invention relates to the use of NK3R antagonists and formulations thereof as described above for the therapeutic or cosmetic treatment of excess body fat and/or of excess body weight, preferably in the therapeutic treatment of excess body fat and/or prevention of body fat gain.

"Therapeutic treatment" should be distinguished from "cosmetic treatment". When not otherwise specified, "treatment" should be understood as "therapeutic treatment". The same applies to related terms "treat" and "treating".

Therapeutic Use

In the context of therapeutic treatment, "excess of body fat and/or of excess body weight" in a patient should be understood as "pathological excess of body fat and/or of excess body weight", i.e. referring to an excess of body fat and/or of excess body weight associated with a growing burden of disease (typically glucose metabolism disorders, insulin resistance, metabolic syndrome, diabetes or vascular disorders); as it is especially the case with abdominal adiposity. Moreover, in this context, "prevention of body fat gain in a patient" should be understood as referring to the prevention of body fat gain wherein if the fat gain had occurred, it would occur an excess of body fat associated with a growing burden of disease (typically glucose metabolism disorders, insulin resistance, metabolic syndrome, diabetes or vascular disorders); as it is especially the case with abdominal adiposity. The term "overweight" is taken to mean the medical condition in which excess body fat has accumulated to the extent that it may have an adverse effect on health, leading to reduced life expectancy and/or increased health problems. Body mass index (BMI), a measurement which compares weight and height, defines people as "overweight" if their BMI is between 25 and 30 kg/m$^2$, and "obese" when it is greater than 30 kg/m$^2$. Therefore, overweight patients are not obese.

In a general meaning, "therapeutic treatment" refers to treatment, prophylactic or preventive measures and deferment of the disease onset; wherein the object is to delay, prevent or slow down (lessen) the targeted pathologic condition or disorder, in a patient. The term "patient" refers to a warm-blooded animal, more preferably a human, who/which is awaiting or receiving medical care or is or will be the object of a medical procedure, or monitored for the development of a disease. Patients include those already with the disorder as well as those prone to have the disorder or those in whom the disorder is to be prevented or delayed.

In one embodiment, "therapeutic treatment" means accomplishing one or more of the following in a patient that is suffering from pathological excess of body fat and/or of excess body weight: (a) reducing the severity of excess body fat and/or of excess body weight; (b) limiting or preventing development of excess body fat and/or of excess body weight; (c) inhibiting worsening of excess body fat and/or of excess body weight; and (d) limiting or preventing recurrence of excess body fat and/or of excess body weight in patients that previously had excess body fat and/or of excess body weight.

In one embodiment, a patient is successfully "treated" if, after receiving a therapeutic amount of the active agent, the patient shows observable and/or measurable stabilization or reduction of body weight and/or body fat mass; and/or relief to some extent of one or more of the symptoms associated with excess body weight and/or excess body fat; reduced morbidity and mortality, and improvement in quality of life issues. The above parameters for assessing successful treatment and improvement in the disease are readily measurable by routine procedures familiar to a skilled artisan.

According to one embodiment, "treating excess body weight" means that the administration of an NK3R antagonist, such as defined herein, and with a dosage determined by the person skilled in the art, makes it possible to reduce the weight of the treated patients. Such NK3R antagonist also enables to prevent weight gain and/or to stabilize a weight as low as possible, and/or to delay the development of excess body weight, especially in patient having a risk of developing excess body weight.

According to one embodiment, "treating excess body fat" means that the administration of an NK3R antagonist, such as defined herein, and with a dosage determined by the person skilled in the art, makes it possible to reduce the body fat of the treated patients. Such NK3R antagonist also enables to prevent the accumulation of body fat and/or to maintain a body fat as reduced as possible, and/or to delay the accumulation of body fat, especially in patient having a risk of developing excess body weight and/or of developing an excess body fat of pathological nature (i.e. associated with a growing burden of disease); as is often the case with abdominal adiposity.

According to one embodiment, "treating excess of body fat and/or of excess body weight" refers to any one or more of treating, preventing, arresting and reducing weight-gain, whereby at least one or more of the following is achieved:
  decrease in body fat and/or body weight, preferably decrease in body fat;
  prevention of weight gain and/or cessation of weight gain;
  decrease or maintenance of plasma triglyceride levels;
  improvement in leptin resistance;
  reduction in hyperglycemia and/or decrease in incidence or severity of diabetes;
  reduction in hyperlipidaemia and/or hypertriglyceridemia;
  decrease in food intake;
  improvement in at least one condition associated with weight gain including a cardiovascular disorder, a sleep disorder, a metabolic condition, a diabetes-related condition;
  at least partial improvement (e.g., termination of or reduction in occurrence) of a condition selected from binge eating disorder, night eating syndrome, obsessive eating, compulsive eating or bulimia.

The present invention thus relates to a NK3R antagonist for use in the treatment of excess body weight and/or excess body fat, especially the treatment of excess body fat and/or the prevention of body fat gain. According to the one embodiment, the invention relates to a NK3R antagonist for use in the therapeutic treatment of pathological excess body weight and/or excess body fat. According to the one embodiment, the invention relates to a pharmaceutical composition comprising a NK3R antagonist for use in the therapeutic treatment of pathological excess body weight and/or excess body fat.

According to one embodiment, the invention relates to the use of a NK3R antagonist in the manufacture of a medicament for the treatment of excess body weight and/or excess body fat. According to a specific embodiment, the invention relates to the use of a NK3R antagonist in the manufacture of a medicament for the treatment of excess body weight and/or excess body fat, comprising the manufacture of tablets comprising the NK3R antagonist. According to a specific embodiment, the invention relates to the use of a NK3R antagonist in the manufacture of a medicament for the treatment of excess body weight and/or excess body fat, comprising the manufacture of capsules comprising the NK3R antagonist. According to a specific embodiment, the invention relates to the use of a NK3R antagonist in the manufacture of a medicament for the treatment of excess body weight and/or excess body fat, comprising the manufacture of sachets of loose powder comprising the NK3R antagonist.

According to one embodiment, the invention relates to a method of treatment of excess body weight and/or excess body fat, comprising the administration of an effective amount of NK3R antagonist to a patient suffering from excess body weight and/or excess body fat, and optional renewal of said administration until the desired therapeutic effect is obtained.

According to one embodiment, the invention also relates to a method of treatment of excess body weight and/or excess body fat, comprising the administration of an effective amount of a pharmaceutical composition comprising a NK3R antagonist, to a patient suffering from excess body weight and/or excess body fat, and optional renewal of said administration until the desired therapeutic effect is obtained.

The term "therapeutically effective amount" (or more simply an "effective amount") as used herein means the amount of active agent (e.g. NK3R antagonist) that is effective for treating pathological excess body fat and/or of excess body weight. The effective amount may vary from patient to patient, depending upon the age, the patient's size and health, the nature and extent of the condition being treated, recommendations of the treating physician, and the therapeutics or combinations of therapeutics selected for administration.

Especially, the invention relates to the treatment and/or prevention of abdominal fat accumulation, the impact of which is highly worrying in terms of morbidity and mortality.

In the treatment of the invention, the body fat loss occurs without any loss of the lean body mass (i.e. with no muscular atrophy), the weight loss is thus essentially associated with a targeted body fat loss.

In the treatment of the invention, the body fat loss occurs without any loss of bone mineral density or bone mineral content, the weight loss is thus essentially associated with a targeted body fat loss.

In the treatment of the invention, the body fat loss occurs without any loss of bone mineral density or bone mineral content and without any loss of the lean body mass (i.e. with no muscular atrophy), the weight loss is thus essentially associated with a targeted body fat loss.

In a particular embodiment, the method of treatment of the invention may comprise the administration of at least one additional active substance for the same therapeutic indication and/or for complementary indications. In a preferred embodiment, the NK3R antagonist is the only substance administered as active substance for treating excess body weight and/or excess body fat.

The therapeutic use of NK3R antagonists according to the present invention is intended for patients that are suffering from pathological excess of body fat and/or of excess body weight, especially for patients that are suffering from pathological excess of body fat. The therapeutic use of NK3R antagonists according to the present invention is also intended for patients that are prone to suffer from pathological excess of body fat and/or of excess body weight, especially for patients that are prone to suffer from pathological excess of body fat. According to a specific embodiment, in the present invention, patients do not suffer from obesity.

The therapeutic use of NK3R antagonists according to the present invention for the treatment of excess body fat and/or the prevention of body fat gain, is intended for patients that are leptin-sensitive patients, preferably leptin sensitive women patients. In this context, according to one embodiment, "leptin-sensitive patients" encompass (i) patients in whom the circulating leptin levels are low (hypoleptinemic state) and (ii) patients in whom the circulating leptin levels are normal but in any case the patients remain in a leptin-sensitive state. In this context, according to a specific embodiment, "leptin-sensitive patients" refers to patients in which a variation of circulating leptin levels has an effect on body fat mass.

According to one embodiment, patients are individuals suffering from hormonal imbalance. According to a specific embodiment, patients are individuals at risk of weight gain due to an anticipated decrease in the levels of the sex hormones (namely, androgens in the case of men and estrogens in the case of women). Specific examples include:
  women subjected to estrogen-lowering therapies, for example in the context of the treatment of breast, cervical, uterine cancers; or for the treatment of women's health disorders such as endometriosis, uterine fibroids, heavy menstrual bleeding and polycystic ovary syndrome (PCOS);
  women experiencing natural, age-related decreases in estrogens as occurring during peri-menopause and post-menopause;
  men subjected to androgen-lowering therapies, for example in the context of the treatment of prostate-cancer or benign prostatic hyperplasia (BPH);
  men experiencing natural, age-related decreases in circulating testosterone.

According to a specific embodiment, patients are women, especially women that undergo changes in ovarian hormone levels.

According to a specific embodiment, patients are women subjected to estrogen-lowering therapies. According to a specific embodiment, patients are women experiencing natural, age-related decreases in estrogens.

According to a specific embodiment, patients are men subjected to androgen-lowering therapies. According to a specific embodiment, patients are men experiencing natural, age-related decreases in circulating testosterone.

According to one embodiment, patients are individuals suffering from genetic susceptibility to excess body weight.

According to one embodiment, patients are individuals where an adipose-specific decrease in weight is deemed to be of therapeutic benefit. Specific examples include overweight individuals; individuals receiving medical treatments that are accompanied with weight gain comprising but not limited to hormonal treatment as well as steroids, pain or antipsychotic medications; individuals having inappropriate eating behaviors.

According to one embodiment, patients are overweight individuals. According to a specific embodiment, patients are not obese. According to one embodiment, patients are individuals receiving medical treatments which can cause weight gain. According to one embodiment, patients are individuals having inappropriate eating behaviors.

The present invention also relates to the use of NK3R antagonists and formulations thereof as described above for increasing circulating leptin levels in a patient in need thereof. According to one embodiment, the invention relates to a NK3R antagonist for use in increasing circulating leptin levels in a patient. According to one embodiment, the invention relates to the use of a NK3R antagonist for the manufacture of a medicament for increasing circulating leptin levels in a patient. The invention also provides a method for increasing circulating leptin levels in a patient comprising the administration of an NK3R antagonist to a patient in need thereof.

The present invention also relates to the use of NK3R antagonists and formulations thereof as described above for the treatment of leptin-related diseases. According to one embodiment, the invention relates to a NK3R antagonist for use in the treatment of a leptin-related disease. According to one embodiment, the invention relates to the use of a NK3R antagonist for the manufacture of a medicament for treating and/or preventing leptin-related diseases. The invention also provides a method of treatment of a leptin-related disease comprising the administration of an NK3R antagonist to a patient in need thereof.

According to one embodiment, a disease is related to leptin when circulating leptin levels are lower compared to healthy subjects. The determination of the circulating leptin levels, especially in blood and/or plasma, may be performed by means known by those skilled in the art, such as for example by enzyme-linked immunosorbent assay (ELISA).

According to an embodiment, a disease is related to leptin when leptin or leptin gene is altered in its structure and thus in its function or when the leptin receptor or leptin receptor gene is altered in its structure and thus in its function, compared to healthy subjects.

According to an embodiment, a "leptin-related disease" is a disease wherein increasing leptin levels may improve or normalize most of patient phenotypes and so is beneficial for the patient. Leptin-related diseases encompass (i) diseases where the circulating leptin levels are low (hypoleptinemic state) and (ii) diseases where the circulating leptin levels are normal but in any case the patients affected by such diseases remain in a leptin-sensitive state.

In one embodiment, the leptin-related disease is selected from metabolic disorders such as diabetes (especially type 1 diabetes), cardiovascular diseases or metabolic syndrome; lipid regulation disorders such as lipodystrophy, including congenital and acquired lipodystrophy, dyslipidemia, non-alcoholic fatty liver disease (NAFLD), nonalcoholic steatohepatitis (NASH) or hyperlipidemia; Congenital Leptin Deficiency (CLD); hypothalamic amenorrhea, including exercise-induced hypothalamic amenorrhea; Rabson-Mendenhall syndrome; osteoporosis.

According to one embodiment, the invention relates to the use of a NK3R antagonist as a leptin replacement therapy in any leptin-sensitive state. In one embodiment, the invention relates to the use of a NK3R antagonist as a substitution product of recombinant leptin, preferably as a substitution product of recombinant methionyl human leptin, more preferably as a substitution product of metreleptin.

Cosmetic Use

The present invention also relates to the use of NK3R antagonists or formulations thereof for the cosmetic treatment of excess body fat and/or of excess body weight in a subject.

In the cosmetic context, "excess of body fat and/or of excess body weight" in a subject should be understood as "unaesthetic excess of body fat and/or of excess body weigh", i.e. referring to an excess body weight or fat accumulation which is not associated with pathological conditions or a growing burden of disease. Such excess body weight or body fat typically exists as cellulite and is preferably distributed according to a gynoid pattern.

The term "subject" refers to a warm-blooded animal, more preferably a human, who/which is in good health, with a normal corpulence, i.e. having a BMI from 18.5 to 25 kg/m$^2$, the excess body weight or fat accumulation of whom is not associated with no pathological conditions or a growing burden of disease (typically glucose metabolism disorders, insulin resistance, metabolic syndrome, diabetes or vascular disorders).

The "cosmetic treatment" is intended to provide an aesthetic/cosmetic effect in subjects, by improving the bodily appearance through stimulating the loss of body weight and/or of body fat. It enables subjects to stabilize weight and to stay thin without localized fat deposits. The cosmetic method according to the invention is especially suited to the reduction of cellulite, in particular on hips and buttock.

The present invention thus relates to a cosmetic treatment method for improving the bodily appearance by stimulating the loss of body weight and/or of body fat in a subject, comprising the administration to said subject of a NK-3 receptor antagonist as defined above, and optionally the renewal of said administration until the expected cosmetic effect is obtained.

According to one embodiment, the present invention also relates to a cosmetic treatment method for improving the bodily appearance by stimulating the loss of body weight and/or of body fat in a subject, comprising the administration to said subject of cosmetic composition comprising a NK-3 receptor antagonist as defined above, and optionally the renewal of said administration until the expected cosmetic effect is obtained.

The cosmetic method of the invention is non-therapeutic.

According to one embodiment, the cosmetic method of the invention is aimed at subjects which are individuals being in good health. Especially, the subjects have a normal corpulence, according to the WHO standards, and thus being not obese.

Advantageously, in the cosmetic method of the invention, the body fat loss occurs without any loss of the lean body mass (i.e. with no muscular atrophy), the weight loss is thus essentially associated with a targeted body fat loss.

According to a specific embodiment, in the cosmetic method of the invention, the NK3R antagonist is adapted to oral administration and is intended to be taken as a food supplement. It may comprise any additional compound with a nutritional interest and/or stimulating weight loss or body fat reduction. It could comprise, for example, vitamins, mineral salts, essential amino acids, essential fatty acids, oligo-elements, various plant extracts, fibers, antioxidants, flavonoids. Natural components may also be mentioned which have anorectic properties.

In a particular embodiment, the NK3R antagonist is the only substance administered as active substance for slimming the figure and/or reducing or restraining localized fat accumulations or lipodystrophia, and/or for stimulating the loss of excess body weight and/or of cellulite, and/or for limiting the accumulation thereof. In another embodiment, the NK3R antagonist is the only substance administered as active substance.

EXAMPLES

The present invention will be better understood with reference to the following examples.

Example 1: Decrease of % Fat/Total Mass in Monkeys

The cynomolgus monkey was selected as a relevant species because of the similarity of nonhuman primates (NHP) to humans. The route of administration is oral consistent with the intended route in humans.

Sexually-mature (age range of ~4 years at pre-dose), purpose-bred cynomolgus monkeys (*Macaca fascicularis*) of Asian origin were used. Sexual maturity was proven by recording of at least two menstrual bleedings (with 20-to-50 days between menstruations) prior to entry into the study.

NHPs were maintained on a standard lab diet of twice-daily offerings of commercial pellets for primates supplemented with fresh fruit and bread. Dietary and environmental enrichment were also provided through the study duration. Animals were housed in a climate (19-25° C.) and humidity (40-70%) controlled environment with artificial lighting controlled automatically to give a cycle of 12 hours light and 12 hours dark.

NHPs were divided into three treatment groups: vehicle control (N=6) and compound k-5 Dose Groups of 10 mg/kg (N=4) and 50 mg/kg (N=6), respectively. All NHPs were dosed once daily (morning) by oral gavage over the 13 week treatment period of the study. The dose vehicle was 0.5% methylcellulose (Methocel® from Colorcon) in water.

All NHPs were subjected to a body weight measurement and DEXA scan (Dual-energy X-ray absorptiometry, Hologic Dexa QDR® 4000) in the pre-dose phase and in the final week (week-13) of the dosing phase. The measurements were made under ketamine anesthesia with dorbene and antisedan.

The whole body was scanned by DEXA for measurement of lean mass, bone mineral density, bone mineral content and fat mass.

All NHPs were subjected to leptin levels measurements. Blood samples were collected at 08h00 in the morning from overnight-fasted animals on Day-2 prior to dosing ('pre-dose'), 24 h after the initial dosing, on day 52 of dosing and on day 86 of dosing. Serum samples were derived from these blood samples and stored frozen (−20° C.) until analysis. Leptin concentrations in these serum samples were determined by ELISA assay (Monkey Kit: MyBiosource Cat. No MBS705354) based upon linear regression analysis against a standard curve.

Figure 3:
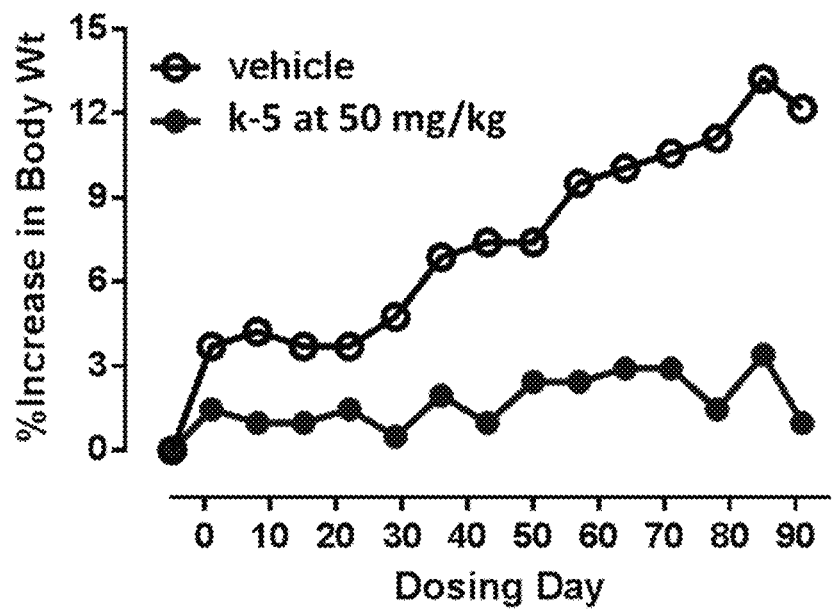
FIG. 3 is a graph showing the percentage of body weight increase along treatment for the vehicle-control group versus treated group with 50 mg/kg of compound k-5.

Effect on body weight: A mean weight gain of about 12% was observed in vehicle-treated monkeys over the course of the dosing phase of the study (FIG. 3). In comparison, there was no significant change in mean weight for the k-5 treated group over the course of the dosing phase of the study.

Figure 1:
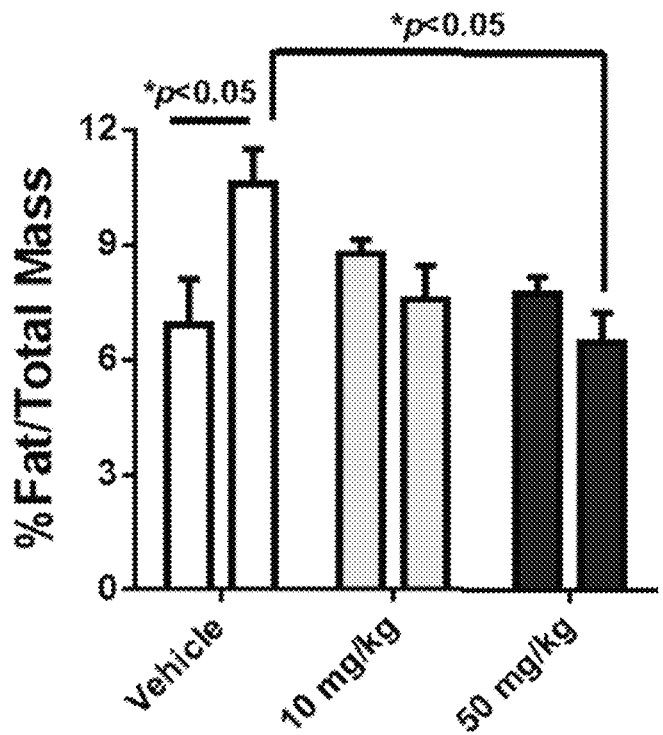
FIG. 1 is a histogram showing the % Fat/Total Mass ratio in the pre-dose phase (left column) versus final week (week-13) of the dosing phase (right column) for each group (vehicle-control group versus treated groups with 10 and 50 mg/kg of compound k-5). Data are presented as mean±SEM; N=4-6/group, stats by 2-way ANOVA, Bonferroni's MCT.

Effects on body composition: There were no significant changes in lean mass, nor bone mineral density not bone mineral content at any measurement, for any group, over the course of the study. DEXA analysis revealed that % fat/total mass increased in the vehicle group over the 13-week study course, as is often observed as NHPs are confined to study. In contrast, no significant change in % fat/total mass was observed in any of the compound k-5 dose groups over the 13-week treatment period, as presented in FIG. 1. A statistically-significant difference was determined between the vehicle-treated and 50 mg/kg-treated groups where N values were 6 subjects/group. In total, these data demonstrate that treatment with compound k-5 prevents adiposity gain in monkeys while not decreasing lean mass.

Figure 2:
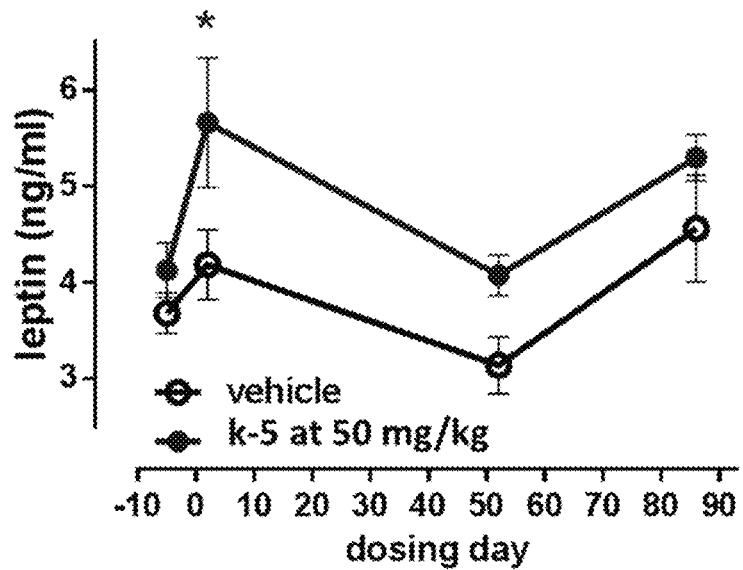
FIG. 2 is a graph showing the plasma leptin level along treatment for the vehicle-control group versus treated group with 50 mg/kg of compound k-5 (*: p<0.05, 2-way ANOVA & Sidak's MCT).

Effects on leptin: FIG. 2 illustrates that compound k-5 treatment significantly increases serum leptin levels 24-hours after initial dosing relative to (a) pre-dose levels within the same group and (b) time-matched levels within the vehicle-treated group. Also, the figure illustrates that serum leptin levels were persistently higher in the k-5-treated group relative to the vehicle-treated group over the duration of dosing.

Study conclusions: Sexually-mature, female monkeys treated with compounds of the invention have decreased weight gain relative to vehicle treated controls. This difference in weight gain is due entirely to a drug-related reduction in % fat mass relative to vehicle controls and not due to changes in bone or muscle density. Moreover, this decrease in % fat mass, relative to vehicle group, correlates with a significant increase in circulating leptin concentrations in response to treatment.

Example 2: Decrease of Total Body Weight in Healthy Women

Multiple Ascending Dose Administration in Healthy Women

Three Panels A, B, and C, each consisting of 6 healthy women, were randomized to receive different dose level of compound k-5. In those 3 panels, compound k-5 is administered for 21 consecutive days.

Subjects were residential from the day before first dosing (D-1) until Day 24 (=72 hours after the last dose intake on Day 21). Weekly non-residential visits were organized on Day 28, Day 35 (±1 day) and a follow-up visit on Day 42 (±2 days). Ascending multiple doses of compound k-5 were administered in a once-daily regimen for 21 consecutive days. The suggested dose levels were: 20 mg, 60 mg and 180 mg based on previous studies. Subjects received the trial medication in a q.d. regimen and after a light breakfast.

Main Criteria for Subject Inclusion

Subjects were recruited on the basis of their medical history and health status. Especially, subjects meeting all of the following criteria were eligible to participate in this study:

1) Premenopausal females between 18 and 45 years of age inclusive.

2) Healthy with no clinically significant abnormalities as determined by medical history, physical examination, blood chemistry assessments, hematologic assessments, coagulation and urinalysis, measurement of vital signs, and ECG. Isolated out-of-range values judged by the physician to be of no clinical significance were allowed. This determination had to be recorded in the subject's source documents.

3) Had a body weight in the range of 50 to 100 kg inclusive.

4) Agreed to abstain from alcohol intake 24 hours before administration of study compound, during the period of the study and 24 hours prior to all other clinic visits.

5) Agreed not to use prescription medications within 14 days prior to study compound administration and through the duration of the study, unless approved by the Investigator and Sponsor medical monitor.

6) Agreed not to use over-the-counter (OTC) medications (including corticosteroids, aspirin, decongestants, antihistamines, and other non-steroidal anti-inflammatory drug [NSAIDs]), and herbal medication (including herbal tea, St. John's Wort), within 14 days prior to study compound administration through the final follow-up visit, unless approved by the investigator and Sponsor medical monitor. Occasional use of paracetamol at recommended doses was allowed.

7) Subjects had to have signed an informed consent document indicating that they understood the purpose of and procedures required for the study and were willing to participate in the study.

8) Willing/able to adhere to the study visit schedule and other requirements, prohibitions and restrictions specified in this protocol.

Weight Measurement

The weight was measured at screening, which took place between 28 and 2 days before start of dosing (D-28 to D-2), and at the end-of-study visit (D42, i.e. 21 days after cessation of study compound intake).

Results

A two-tailed T-test for paired samples was used to explore the difference between the screening and post-study values for weight. Mean values per dose group are tabulated in the following table:

| Dose group | Weight Screening (kg) | Weight D 42 (kg) | Pre vs Post Difference (kg) | Pre vs Post Difference (%) | Matching p-value |
|---|---|---|---|---|---|
| Cpd k-5 20 mg | 58.2 | 58.0 | −0.13 | −0.23% | 0.70 |
| Cpd k-5 60 mg | 73.3 | 71.9 | −1.38 | −1.92% | 0.15 |
| Cpd k-5 180 mg | 69.0 | 66.9 | −2.10 | −3.14% | <0.02 |

Based on these results it can be concluded that a dose-dependent trend exists towards weight lowering with increasing doses of compound k-5, reaching a significance level of 0.02 in the highest dose group tested in healthy women.

Example 3: Decrease of Body Weight in Healthy Women with Normal Corpulence

Healthy women with normal corpulence, i.e. having a BMI ranging from 18.5 to 25 kg/m$^2$, received 60 mg of compound k-5 for 21 consecutive days.

The weight was measured at screening which took place between 28 and 2 days before start of dosing (D-28 to D-2), as well as on the follow-up visit planned on D42 (21 days after cessation of study compound intake).

Weight and BMI before and after dosing are presented below:

| Subject | Height (cm) | Weight Screening (kg) | Weight D42 (kg) | Difference (kg) | Difference (%) | BMI screening | BMI D42 |
|---|---|---|---|---|---|---|---|
| 1 | 173 | 66.4 | 64.2 | −2.2 | −3.43% | 22.18 | 21.45 |
| 2 | 163 | 63 | 61 | −2 | −3.28% | 23.71 | 22.95 |
| 3 | 178 | 68.3 | 67.8 | −0.5 | −0.74% | 21.55 | 21.39 |

These results evidence that the use of a NK3R antagonist enables lowering weight in healthy women.

Example 4: Decrease of Body Weight in Overweight Women

Overweight women, i.e. having a BMI ranging from 25 to 30 kg/m$^2$, received 180 mg of compound k-5 for 21 consecutive days.

The weight was measured at screening which took place between 28 and 2 days before start of dosing (D-28 to D-2), as well as on the follow-up visit planned on D42 (21 days after cessation of study compound intake).

Weight and BMI before and after dosing are presented below:

| Subject | Height (cm) | Weight Screening (kg) | Weight D42 (kg) | Difference (kg) | Difference (%) | BMI screening | BMI D42 |
|---|---|---|---|---|---|---|---|
| 4 | 156 | 68 | 65.2 | −2.8 | −4.29% | 27.94 | 26.79 |
| 5 | 160 | 71.2 | 67 | −4.2 | −6.27% | 27.81 | 26.17 |
| 6 | 179 | 87 | 84 | −3 | −3.57% | 27.15 | 26.21 |

These results evidence that the use of a NK3R antagonist enables lowering weight in overweight women.

Example 5: Effect on Plasma Leptin Level in Women

This was a randomized, double-blind, placebo-controlled study. All subjects provided written informed consent prior to screening for study eligibility. Healthy female volunteers aged 20-45 years with a body mass index of 19-30 kg/m$^2$ were included. Participants needed to be in good physical health including the presence of a regular ovulatory menstrual cycle and the discontinuation of all hormonal contraceptive methods at least 3 months prior to screening. Three panels of 8 non-obese female volunteers (median BMI of each panel: 22.3, 23.4, 25.2 kg/m$^2$) each were administered capsules of compound k-5 or matching placebo in a 6:2 ratio for 21 days. Subjects received the study medication in a once daily regimen after a light standardized breakfast. The participants in these panels were synchronized for their menstrual cycle; i.e. the initiation of dosing was always on Day3 ±2 of the menstrual cycle. The dose levels investigated were 20, 60 and 180 mg of compound k-5. Blood samples were collected on the day prior to dosing as well as on Day 21 (the final day of dosing) and plasma fractions were retained and stored frozen (−20° C.) until analysis. Leptin concentrations in these plasma samples were determined by ELISA assay (Human Leptin Kit: R&D Systems, Cat. No DLP00) based upon linear regression analysis against a standard curve.

Figure 4:
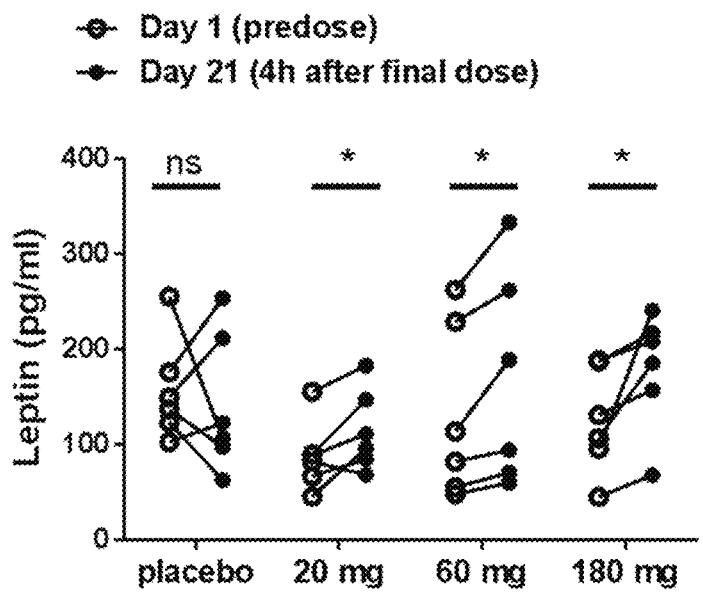
FIG. 4 is a diagram showing plasma leptin level in the pre-dose phase versus 4 h after final dose, for each group (placebo group versus treated groups with 20, 60 and 180 mg of compound k-5) (*p<0.05; paired t-test).

Effects on Leptin: FIG. 4 illustrates that compound k-5 treatment significantly (*$p<0.05$; paired t-test) increases serum leptin levels in women at all dose levels following 21 days of treatment relative to pre-dose levels. In comparison, placebo treatment had no significant effect on plasma leptin levels.

Study Conclusion: Compound k-5 increases circulating leptin levels in non-obese, premenopausal women. As leptin is a hormone known to have effects on weight gain and adiposity, these results may be relevant to % fat density relative to overall body composition, analogous to the data presented above for female, non-human primates (example 1).

Example 6: Effect on Plasma Leptin Level in Female Rats Over the Estrous Cycle Rats do not have a menstrual cycle, but rather an estrous cycle that can be clearly defined by peak estrogen levels (precluding ovulation) that occurs regularly over a period of ~4 days.

Daily plasma samples were collected each morning from sexually-mature female rats and analyzed for peak estrogen levels (coincident with proestrus) in order to define the timing of the estrous cycle for individual rats.

Next, rats were dosed orally BID (i.e. twice a day) with vehicle (0.5% methylcellulose) over a 4-day 'baseline' estrous cycle. Plasma samples were collected daily, each morning, and stored frozen prior to analysis for leptin.

Then, the rats were separated into two groups treated with either compound k-5 10 mg/kg, oral BID, or with vehicle over the 4-day 'treatment' estrous cycle. Plasma samples were collected daily, each morning, and stored frozen prior to analysis for leptin.

In a single experiment, plasma samples collected daily during both the 'baseline' and 'treatment' cycles were analyzed in a common experiment by ELISA assay based upon linear regression analysis against a standard curve. Leptin levels over the 4-day estrous cycle were calculated for individual rats by determination of AUC (area-under-the-curve) using credited data analysis software (GraphPad Prism).

Figure 5:
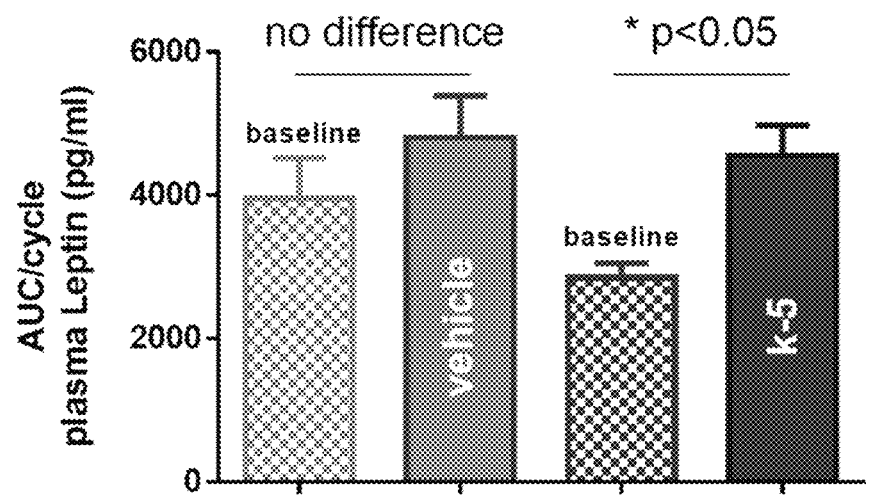
FIG. 5 is a histogram showing plasma leptin level in baseline estrous cycle (left column) versus treatment estrous cycle (right column) for each group (vehicle-control group versus treated group with 10 mg/Kg of compound k-5) (*p<0.05, paired t-test).

Effects on Leptin: FIG. 5 illustrates that compound k-5 treatment significantly (*p<0.05; paired t-test) increases plasma leptin levels in female rats over the 4-day estrous cycle compared to when the same rats were treated with vehicle in the 'baseline' cycle.

Study Conclusion: Compound k-5 treatment increases circulating leptin levels in non-obese, sexually-mature female rats over the estrous cycle. As leptin is a hormone known to have effects on weight gain and adiposity, this finding may be relevant to % fat density relative to overall body composition, analogous to the data presented above for female, non-human primates (example 1) and in women (example 5).

The invention claimed is:

1. A method for increasing circulating leptin levels in a patient in need thereof, comprising:
   determining that the circulating leptin levels in said patient are low compared to a healthy subject;
   administering an NK-3 receptor antagonist to a patient in need thereof, wherein the NK-3 receptor antagonist is of general formula III:

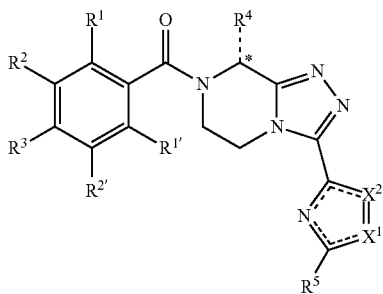

or a pharmaceutically acceptable solvate thereof, wherein:
   $R^1$ is H, F or methyl;
   $R^{1'}$ is H;
   $R^2$ is H, F, Cl or methoxy;
   $R^{2'}$ is H or F;
   $R^3$ is H, F, Cl, methyl, trifluoromethyl, nitrile or $R^3$ is thiophen-2-yl under the condition that $R^5$ is not methyl;
   $R^4$ is methyl, ethyl, n-propyl, hydroxyethyl, methoxyethyl, trifluoromethyl, difluoromethyl or fluoromethyl;
   $R^5$ is methyl, ethyl, methoxymethyl, trifluoromethyl, difluoromethyl, fluoromethyl, 1-fluoroethyl, 1,1-difluoromethyl or 2,2,2-trifluoroethyl;
   $X^2$ is N and $X^2$ is S or O; $X^1$ is S and $X^2$ is N;
   *** represents a single or a double bond depending on $X^1$ and $X^2$; and
   *--- stands for the (R)-enantiomer or for the racemate compound of formula III, and
   wherein said administration increases circulating leptin levels in said patient.

2. The method according to claim 1, wherein said patient has a disease selected from the group consisting of metabolic disorders; lipid regulation disorders; Congenital Leptin Deficiency; hypothalamic amenorrhea; Rabson-Mendenhall syndrome; and osteoporosis.

3. The method according to claim 1, wherein said patient has a disease selected from the group consisting of diabetes, cardiovascular diseases, and metabolic syndrome.

4. The method according to claim 1, wherein said patient has a disease selected from the group consisting of lipodystrophy, dyslipidemia, nonalcoholic fatty liver disease, non-alcoholic steatohepatitis, and hyperlipidemia.

5. The method according to claim 1, wherein said patient has a disease selected from the group consisting of congenital lipodystrophy, acquired lipodystrophy, and exercise-induced hypothalamic amenorrhea.

6. The method according to claim 1, wherein the NK-3 receptor antagonist is administrated under the form of a pharmaceutical composition comprising the NK-3 receptor antagonist and at least one pharmaceutically acceptable vehicle.

7. The method according to claim 1, wherein the NK-3 receptor antagonist is (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone, or a pharmaceutically acceptable solvate thereof.

8. The method according to claim 1, wherein the NK-3 receptor antagonist is (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone.

* * * * *

UNITED STATES PATENT AND TRADEMARK OFFICE
CERTIFICATE OF CORRECTION

PATENT NO.         : 11,478,472 B2                                              Page 1 of 1
APPLICATION NO.    : 16/796422
DATED              : October 25, 2022
INVENTOR(S)        : Hamid Hoveyda et al.

It is certified that error appears in the above-identified patent and that said Letters Patent is hereby corrected as shown below:

In the Claims

In Column 57, Claim 1, Line 50, please replace " 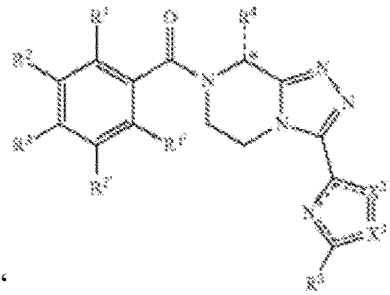 " with

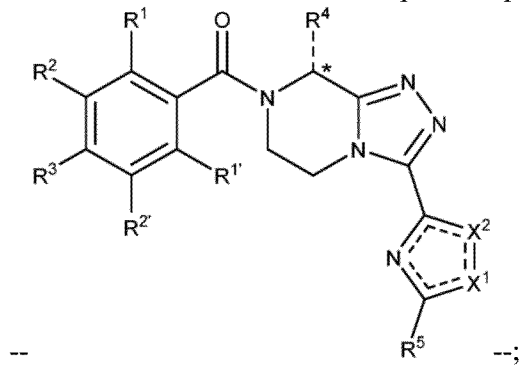

-- --;

In Column 58, Claim 1, Line 17, please replace "$X^2$ is N and $X^2$ is S or O; or $X^1$ is S and $X^2$ is N;" with -- $X^1$ is N and $X^2$ is S or O; or $X^1$ is S and $X^2$ is N; --;

In Column 58, Claim 1, Line 18, please replace "***" with -- ==== --.

Signed and Sealed this
Thirtieth Day of July, 2024

*Katherine Kelly Vidal*

Katherine Kelly Vidal
*Director of the United States Patent and Trademark Office*